US012282871B2

(12) United States Patent
Komikawa et al.

(10) Patent No.: US 12,282,871 B2
(45) Date of Patent: Apr. 22, 2025

(54) INFORMATION PROCESSING APPARATUS, INFORMATION PROCESSING METHOD, AND PROGRAM

(71) Applicant: FUJIFILM Corporation, Tokyo (JP)

(72) Inventors: Takumi Komikawa, Kanagawa (JP); Masataka Hasegawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 356 days.

(21) Appl. No.: 17/836,716

(22) Filed: Jun. 9, 2022

(65) Prior Publication Data

US 2022/0405654 A1 Dec. 22, 2022

(30) Foreign Application Priority Data

Jun. 18, 2021 (JP) .................... 2021-101863

(51) Int. Cl.
*G06Q 10/04* (2023.01)
*G06N 5/022* (2023.01)
*G06Q 10/0639* (2023.01)
*G16C 60/00* (2019.01)

(52) U.S. Cl.
CPC ............ *G06Q 10/04* (2013.01); *G06N 5/022* (2013.01); *G06Q 10/06395* (2013.01); *G16C 60/00* (2019.02)

(58) Field of Classification Search
CPC .. G06N 5/022; G06Q 10/04; G06Q 10/06395; G16C 60/00; G16C 20/30; G16C 20/70
USPC .......................................................... 702/22
See application file for complete search history.

(56) References Cited

U.S. PATENT DOCUMENTS

2020/0024712 A1 1/2020 Iwamura
2021/0319364 A1* 10/2021 Fujita ...................... G06N 3/045
(Continued)

FOREIGN PATENT DOCUMENTS

JP 2009-044974 A 3/2009
JP 2018-018354 A 2/2018
(Continued)

OTHER PUBLICATIONS

Watanabe et al. WO-2020008654 A1, "Sample Analysis Device and Program for Sample Analysis", Date published: Jan. 9, 2020 (Year: 2020).*
(Continued)

*Primary Examiner* — John H Le
(74) *Attorney, Agent, or Firm* — Studebaker Brackett PLLC

(57) ABSTRACT

The information processing apparatus, the information processing method, and the program include at least one processor configured to acquire, in at least one piece of processing of the process, at least one piece of information of chemical information or physical information of an object to be processed and a processed object at two points at which elapses of processing times between before the processing and after the processing are different from each other, acquire a calculation value of a difference between numerical values at the two points that are obtained from the information, and set the difference as an explanatory variable, set the quality of the product as an objective variable, and predict the quality of the product based on the calculation value by using a trained model obtained by performing machine learning based on a known data set of the explanatory variable and the objective variable.

12 Claims, 24 Drawing Sheets

(56) References Cited

U.S. PATENT DOCUMENTS

| | | | |
|---|---|---|---|
| 2021/0405004 A1* | 12/2021 | Eto | G06N 5/04 |
| 2022/0091589 A1 | 3/2022 | Hasegawa | |
| 2022/0404332 A1* | 12/2022 | Powell | G01N 33/2888 |

FOREIGN PATENT DOCUMENTS

| | | |
|---|---|---|
| WO | 2018/062398 A1 | 4/2018 |
| WO | 2020/058237 A2 | 3/2020 |
| WO | 2021/002110 A1 | 1/2021 |

OTHER PUBLICATIONS

Ren Lei et al., "A Data-Driven Approach of Product Quality Prediction for Complex Production Systems", IEEE Transactions on Industrial Informatics, vol. 17, No. 9, Jun. 9, 2020, pp. 6457-6465, IEEE.

Wang Kai et al., "Deep Learning of Complex Batch Process Data and Its Application on Quality Prediction", IEEE Transactions on Industrial Informatics, vol. 16, No. 12, Nov. 26, 2018, pp. 7233-7242, IEEE.

Lieber Daniel et al., "Quality Prediction in Interlinked Manufacturing Processes based on Supervised & Unsupervised Machine Learning", Procedia CIRP, vol. 7, Jan. 1, 2013, pp. 193-198, Elsevier.

The extended European search report issued by the European Patent Office on Dec. 6, 2022, which corresponds to European Application No. 22178138.8-1111 and is related to U.S. Appl. No. 17/836,716.

An Office Action; "Notice of Reasons for Refusal," mailed by the Japanese Patent Office on Dec. 3, 2024, which corresponds to Japanese Patent Application No. 2021-101863 and is related to U.S. Appl. No. 17/836,716; with English language translation.

* cited by examiner

FIG. 22

| LEVEL NUMBER | INFORMATION DATA INFRARED SPECTROSCOPIC SPECTRUM ||||||||||
|---|---|---|---|---|---|---|---|---|---|---|
| | $a_2$ POINT ||||| $d_2$ POINT |||||
| | PEAK A | PEAK B | PEAK C | ... | PEAK N | PEAK A | PEAK B | PEAK C | ... | PEAK N |
| 1 | 0.059 | 1.843 | 0.912 | ... | 0.033 | 0.721 | 2.314 | 1.286 | ... | 2.793 |
| 2 | 0.084 | 1.665 | 0.867 | ... | 0.052 | 0.451 | 3.198 | 1.627 | ... | 1.318 |
| 3 | 0.195 | 1.110 | 0.638 | ... | 0.089 | 1.079 | 3.109 | 2.053 | ... | 1.414 |
| 4 | 0.074 | 1.735 | 0.318 | ... | 0.005 | 0.753 | 0.856 | 1.125 | ... | 1.556 |
| 5 | 0.092 | 0.489 | 0.862 | ... | 0.098 | 1.438 | 1.865 | 1.335 | ... | 1.333 |
| 6 | 0.091 | 0.906 | 0.527 | ... | 0.105 | 1.126 | 1.258 | 1.456 | ... | 2.512 |
| 7 | 0.105 | 1.210 | 0.608 | ... | 0.135 | 1.456 | 1.556 | 0.963 | ... | 1.385 |
| 8 | 0.351 | 0.556 | 0.379 | ... | 0.096 | 1.221 | 1.325 | 0.854 | ... | 2.109 |
| 9 | 0.062 | 0.742 | 0.816 | ... | 0.176 | 1.663 | 2.257 | 0.254 | ... | 1.835 |
| 10 | 0.295 | 1.092 | 0.638 | ... | 0.054 | 0.837 | 1.416 | 1.051 | ... | 2.945 |

FIG. 23

| LEVEL NUMBER | EXPLANATORY VARIABLE ||||| OBJECTIVE VARIABLE |
| | CALCULATION VALUE DATA OF DIFFERENCE ||||| QUALITY |
| | PEAK A | PEAK C | PEAK C | ... | PEAK N | NUMBER-AVERAGE MOLECULAR WEIGHT |
|---|---|---|---|---|---|---|
| 1 | 0.662 | 0.471 | 0.374 | ... | 2.760 | 27000 |
| 2 | 0.367 | 1.533 | 0.760 | ... | 1.266 | 21340 |
| 3 | 0.884 | 1.999 | 1.415 | ... | 1.325 | 22000 |
| 4 | 0.679 | -0.879 | 0.807 | ... | 1.551 | 24800 |
| 5 | 1.346 | 1.376 | 0.473 | ... | 1.235 | 18500 |
| 6 | 1.035 | 0.352 | 0.929 | ... | 2.407 | 23500 |
| 7 | 1.351 | 0.346 | 0.355 | ... | 1.250 | 14600 |
| 8 | 0.870 | 0.769 | 0.475 | ... | 2.013 | 23300 |
| 9 | 1.601 | 1.515 | -0.562 | ... | 1.659 | 25320 |
| 10 | 0.542 | 0.324 | 0.413 | ... | 2.891 | 11560 |

FIG. 24

| LEVEL NUMBER | INFORMATION DATA MIXING RATIO | | EXPLANATORY VARIABLE | OBJECTIVE VARIABLE |
|---|---|---|---|---|
| | $b_i$ POINT | $d_i$ POINT | CALCULATION VALUE DATA OF DIFFERENCE | QUALITY |
| | MIXING RATIO | MIXING RATIO | | NUMBER-AVERAGE MOLECULAR WEIGHT |
| 1 | 0.38 | 1.00 | 0.62 | 27000 |
| 2 | 0.43 | 0.95 | 0.52 | 21340 |
| 3 | 0.09 | 0.96 | 0.87 | 22000 |
| 4 | 0.15 | 0.98 | 0.83 | 24800 |
| 5 | 0.35 | 0.99 | 0.64 | 18500 |
| 6 | 0.27 | 0.87 | 0.60 | 23500 |
| 7 | 0.25 | 0.79 | 0.54 | 14600 |
| 8 | 0.18 | 0.93 | 0.75 | 23300 |
| 9 | 0.23 | 0.88 | 0.65 | 25320 |
| 10 | 0.26 | 0.85 | 0.59 | 11560 |

FIG. 25

| LEVEL NUMBER | EXPLANATORY VARIABLE ||||||| OBJECTIVE VARIABLE |
| | PROCESSING CONDITION DATA ||||||| |
| | FIRST RAW MATERIAL RM1 || SECOND RAW MATERIAL RM2 || DIAMETER OF REACTION PATH φ | LENGTH OF REACTION PATH L | REACTION TEMPERATURE | NUMBER-AVERAGE MOLECULAR WEIGHT |
| | CONCENTRATION | FLOW VELOCITY | CONCENTRATION | FLOW VELOCITY | | | | |
| | mM | mL/min | mM | mL/min | mm | mm | °C | |
| 1 | 20.0 | 1.0 | 20.0 | 0.6 | 1.0 | 800.0 | 0.0 | 27000 |
| 2 | 20.0 | 2.0 | 20.0 | 1.1 | 1.0 | 600.0 | 5.0 | 21340 |
| 3 | 20.0 | 10.0 | 20.0 | 5.5 | 2.0 | 700.0 | 10.0 | 22000 |
| 4 | 18.0 | 11.0 | 10.0 | 1.1 | 2.0 | 700.0 | 10.0 | 24800 |
| 5 | 20.0 | 0.5 | 20.0 | 1.1 | 2.0 | 700.0 | 10.0 | 18500 |
| 6 | 18.0 | 0.5 | 20.0 | 0.6 | 3.0 | 700.0 | 10.0 | 23500 |
| 7 | 18.0 | 0.5 | 20.0 | 2.0 | 1.0 | 600.0 | 10.0 | 14600 |
| 8 | 18.0 | 0.5 | 10.0 | 2.0 | 1.0 | 500.0 | 10.0 | 23300 |
| 9 | 18.0 | 20.0 | 20.0 | 2.0 | 1.0 | 500.0 | 10.0 | 25320 |
| 10 | 20.0 | 1.0 | 20.0 | 0.6 | 1.0 | 500.0 | 0.0 | 11560 |

FIG. 26

| | EXPLANATORY VARIABLE | | DETERMINATION COEFFICIENT |
|---|---|---|---|
| EXAMPLE 1 | CALCULATION VALUE DATA OF DIFFERENCE (INFRARED SPECTROSCOPIC SPECTRUM) | - | 0.628 |
| COMPARATIVE EXAMPLE 1 | INTEGRATED INTENSITY AT $d_2$ POINT | - | 0.127 |
| EXAMPLE 2 | CALCULATION VALUE DATA OF DIFFERENCE (INFRARED SPECTROSCOPIC SPECTRUM) | PROCESSING CONDITION DATA | 0.773 |
| COMPARATIVE EXAMPLE 2 | INTEGRATED INTENSITY AT $d_2$ POINT | | 0.657 |
| EXAMPLE 3 | CALCULATION VALUE DATA OF DIFFERENCE (COMPUTATIONAL FLUID DYNAMICS ANALYSIS) | PROCESSING CONDITION DATA | 0.614 |
| COMPARATIVE EXAMPLE 3 | MIXING RATIO AT $a_i$ POINT | | 0.491 |

INFORMATION PROCESSING APPARATUS, INFORMATION PROCESSING METHOD, AND PROGRAM

CROSS-REFERENCE TO RELATED APPLICATION

This application claims priority from Japanese Patent Application No. 2021-101863, filed on Jun. 18, 2021, the disclosure of which is incorporated by reference herein in its entirety.

BACKGROUND

Field of the Invention

The present disclosure relates to an information processing apparatus, an information processing method, and a program.

Related Art

A quality of a product is predicted using a machine learning model. For example, in order to improve accuracy of prediction, JP2018-018354A proposes a machine learning model that learns, as learning input data, physical-property relevance data derived from physical-property data representing a physical property of a product.

In related art, various techniques such as JP2018-018354A and the like have been studied. However, at present, accuracy of prediction of a quality of a product is not sufficient.

SUMMARY

The present disclosure has been made in view of such circumstances, and an object of an embodiment of the present disclosure is to provide an information processing apparatus that predicts a quality of a product obtained by a process including one or more pieces of processing with high accuracy.

An object of another embodiment of the present disclosure is to provide an information processing method of predicting a quality of a product obtained by a process including one or more pieces of processing with high accuracy.

An object of still another embodiment of the present disclosure is to provide a program causing a computer to execute information processing of predicting a quality of a product obtained by a process including one or more pieces of processing with high accuracy.

The present disclosure includes the following aspects.

<1> An information processing apparatus that predicts a quality of a product obtained by a process including one or more pieces of processing, the apparatus including: at least one processor configured to acquire, in at least one piece of processing of the process, at least one piece of information of chemical information or physical information of an object to be processed and a processed object at two points at which elapses of processing times between before the processing and after the processing are different from each other, acquire a calculation value of a difference between numerical values at the two points that are obtained from the information, and set the difference as an explanatory variable, set the quality of the product as an objective variable, and predict the quality of the product based on the calculation value by using a trained model obtained by performing machine learning based on a known data set of the explanatory variable and the objective variable.

<2> The information processing apparatus according to <1>, in which the processor is configured to acquire a condition value of a processing condition for the at least one piece of processing of the process, set the explanatory variable to include the processing condition in addition to the difference, and predict the quality of the product based on the calculation value and the condition value in the prediction of the quality of the product.

<3> The information processing apparatus according to <1> or <2>, in which the processor is configured to acquire, in the acquisition of the information, a spectroscopic spectrum as the chemical information in the at least one piece of processing of the process.

<4> The information processing apparatus according to <3>, in which the processor is configured to acquire, in the acquisition of the calculation value, the calculation value of an intensity at a wave number or the calculation value of an integrated intensity in a wave number region, the wave number and the wave number region being a characteristic wave number and a characteristic wave number region in the spectral spectrum changed by the at least one piece of processing.

<5> The information processing apparatus according to <4>, in which the processor is configured to determine the wave number or the wave number region based on a quantum chemical calculation.

<6> The information processing apparatus according to <4> or <5>, in which the characteristic wave number or the characteristic wave number region includes a wave number or a wave number region derived from a by-product.

<7> The information processing apparatus according to any one of <1> to <6>, in which the at least one piece of processing of the process is flow processing using a flow path, and the processor is configured to acquire, in the acquisition of the information, a state quantity of a flow field as the physical information of the flow processing.

<8> The information processing apparatus according to <7>, in which the processor is configured to acquire, in the acquisition of the information, the state quantity of the flow field by a computational fluid dynamics analysis.

<9> The information processing apparatus according to <8>, in which the flow processing is processing of mixing a plurality of fluids, and the state quantity of the flow field is a mixing ratio of the fluids that is calculated based on the computational fluid dynamics analysis.

<10> An information processing method that predicts a quality of a product obtained by a process including one or more pieces of processing, the method including: acquiring, in at least one piece of processing of the process, at least one piece of information of chemical information or physical information of an object to be processed and a processed object at two points at which elapses of processing times between before the processing and after the processing are different from each other; acquiring a calculation value of a difference between numerical values at the two points that are obtained from the information; and setting the difference as an explanatory variable, setting the quality of the product as an objective variable, and predicting the quality of the product based on the calculation value by using a trained model obtained by performing machine learning based on a known data set of the explanatory variable and the objective variable.

<11> A program causing a computer to execute information processing of predicting a quality of a product obtained by a process including one or more pieces of processing, the information processing including: acquiring, in at least one piece of processing of the process, at least one piece of information of chemical information or physical information of an object to be processed and a processed object at two points at which elapses of processing times between before the processing and after the processing are different from each other; acquiring a calculation value of a difference between numerical values at the two points that are obtained from the information; and setting the difference as an explanatory variable, setting the quality of the product as an objective variable, and predicting the quality of the product based on the calculation value by using a trained model obtained by performing machine learning based on a known data set of the explanatory variable and the objective variable.

According to an embodiment of the present disclosure, there is provided an information processing apparatus that predicts a quality of a product obtained by a process including one or more pieces of processing with high accuracy.

According to another embodiment of the present disclosure, there is provided an information processing method of predicting a quality of a product obtained by a process including one or more pieces of processing with high accuracy.

According to still another embodiment of the present disclosure, there is provided a program causing a computer to execute information processing of predicting a quality of a product obtained by a process including one or more pieces of processing with high accuracy.

BRIEF DESCRIPTION OF THE DRAWINGS

FIG. 22 is a table illustrating information data of infrared spectroscopic spectra.

FIG. 23 is a table illustrating calculation value data acquired based on the information data of the infrared spectroscopic spectra.

FIG. 24 is a table illustrating information data of a state quantity of a flow field and calculation value data acquired based on the information data.

FIG. 25 is a table illustrating processing condition data.

FIG. 26 is a table illustrating a determination coefficient.

DETAILED DESCRIPTION

Figure 1:
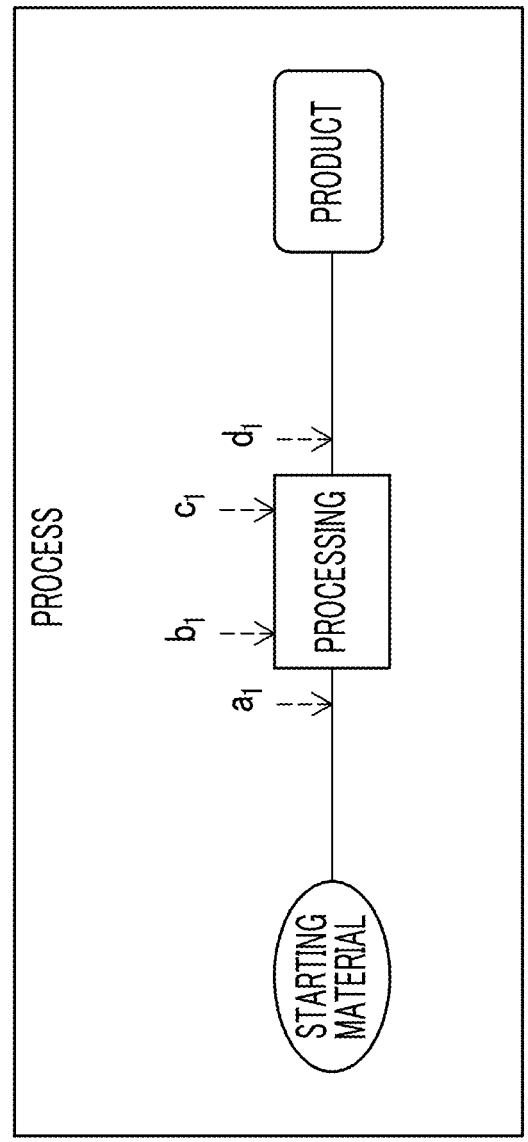
FIG. 1 is a diagram illustrating a process including one piece of processing.

Hereinafter, an information processing apparatus, an information processing method, and a program according to the present disclosure will be described in detail.

In the present disclosure, "A and/or B" is synonymous with "at least one of A or B.". That is, "A and/or B" means that only A may be included, that only B may be included, or that a combination of A and B may be included. Further, in this specification, even in a case where three or more matters are expressed by being connected using "and/or", the same concept as "A and/or B" is applied.

The drawings referred to in the following description are exemplary and are schematically illustrated, and the present disclosure is not limited to these drawings. The same components are denoted by the same reference numerals. Further, the reference numerals in the drawings may be omitted.

Information Processing Apparatus

According to the present disclosure, there is provided an information processing apparatus that predicts a quality of a product obtained by a process including one or more pieces of processing, the apparatus including: at least one processor configured to acquire, in at least one piece of processing of the process, at least one piece of information of chemical information or physical information of an object to be processed and a processed object at two points at which elapses of processing times between before the processing and after the processing are different from each other (hereinafter, may be simply referred to as "acquisition of information"), acquire a calculation value of a difference between numerical values at the two points that are obtained from the information (hereinafter, may be simply referred to as "acquisition of calculation value"), and set the difference as an explanatory variable, set the quality of the product as an objective variable, and predict the quality of the product based on the calculation value by using a trained model obtained by performing machine learning based on a known data set of the explanatory variable and the objective variable (hereinafter, may be simply referred to as "prediction of quality").

In JP2018-018354A, in order to predict a quality of a product, a trained model obtained by performing machine learning based on physical-property data such as spectral spectrum data obtained from the product and the quality of the product is used. On the other hand, in such a method, accuracy of product quality prediction may be lowered.

In this regard, in the information processing apparatus according to the present disclosure, in processing of a process of producing a product, at least one piece of chemical information or physical information is acquired from an object to be processed and a processed object at two points at which elapses of processing times between before and after the processing are different from each other. The information processing apparatus according to the present disclosure predicts a quality of a product by using a trained model obtained by performing machine learning based on a calculation value obtained from the acquired information and the quality of the product. Thereby, it is possible to predict the quality of the product with high accuracy.

Process Including One or More Pieces of Processing

The information processing apparatus includes at least one processor and predicts a quality of a product obtained by a process including one or more pieces of processing.

As illustrated in FIG. 1, examples of the process include a process of obtaining a product by performing one piece of processing on a starting material. Further, as illustrated in FIG. 2, examples of the process include a process of obtaining a product by sequentially performing processing from first processing to n-th processing (n is an integer of 2 or more) on a starting material.

Examples of the starting material include a raw material of a product, an intermediate of a product, and the like.

Figure 2:
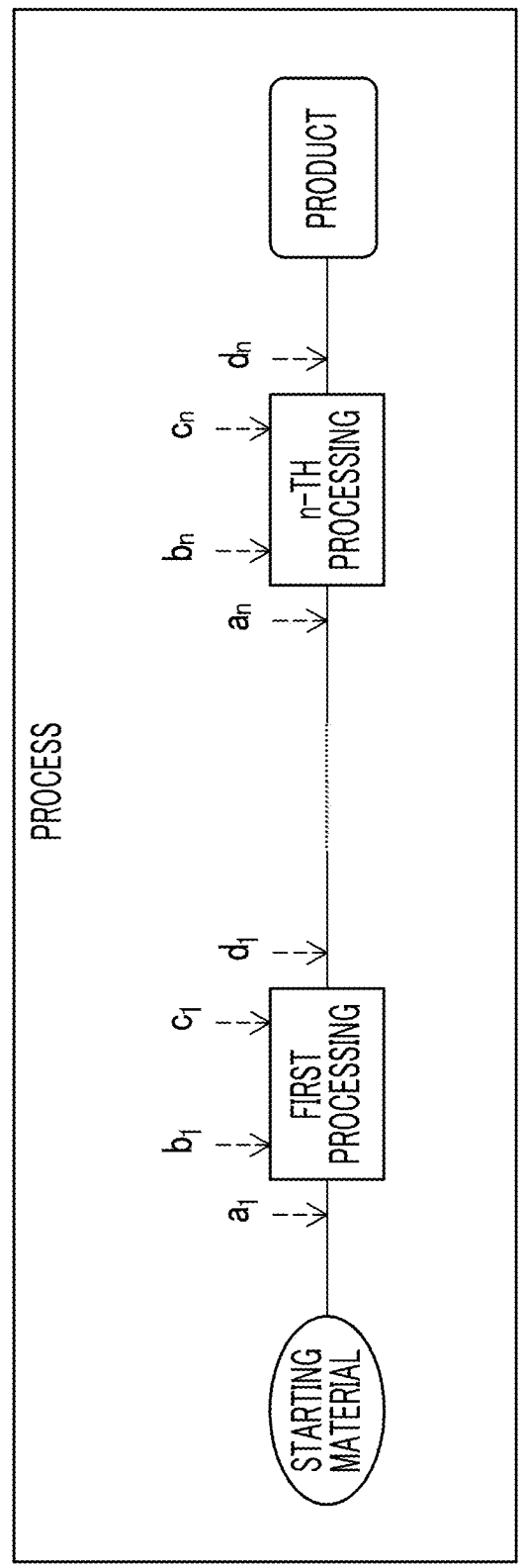
FIG. 2 is a diagram illustrating a process including a plurality of pieces of processing.

The process as illustrated in FIG. 2 may be a continuous process in which pieces of processing are continuously performed, or may be a process including batch processing. The continuous process is preferable because production of a product can be performed while predicting a quality of the product in in-line. For example, a production speed can be improved and quality control can be performed at the same time.

In this specification, "processing" means an operation for causing at least one of a chemical change or a physical change of an object provided for processing.

Examples of the processing include a chemical operation and a physical operation, such as a chemical reaction, heating, cooling, mixing, separation, formation, defoaming, compression, concentration, removal, adsorption, desorption, electrolysis, reflux, stretching, coating, drying, swelling, evaporation, condensation, melting, coagulation, sublimation, dissolution, recrystallization, plasma processing, chromatography, and the like.

By performing a plurality of pieces of processing at the same time, these pieces of processing may be treated as one piece of processing. Further, one piece of processing may substantially involve a plurality of pieces of processing.

The processing may be classified into one of a chemical operation and a physical operation. On the other hand, for example, heating may be processing of applying heat to an object provided for processing to cause a physical change, and at the same time, progressing a chemical reaction to cause a chemical change. Therefore, the processing does not necessarily have to be classified into either a chemical operation or a physical operation, and may be treated as corresponding to both a chemical operation and a physical operation. In addition, the change made by the processing does not necessarily have to be classified into either a chemical change or a physical change, and may be treated as corresponding to both a chemical change and a physical change.

One or a plurality of products may be provided. For example, in a case where a plurality of compounds are obtained by a chemical reaction, one compound may be used as a product and a quality of the product may be predicted, or the plurality of compounds may be used as products and qualities of the products may be predicted.

Further, in the qualities of the products, one quality may be predicted, or a plurality of qualities may be predicted.

Specific examples of the process include a process including flow processing. More specifically, examples of the process include a process including first flow processing of mixing a plurality of raw materials and second flow processing of heating and polymerizing the mixed raw materials (hereinafter, may be referred to as a "polymer synthesis process"). Thereby, it is possible to obtain a polymer as a product.

Examples of a quality of the product (that is, polymer) include a number-average molecular weight, a weight-average molecular weight, a molecular weight dispersion, a yield, a purity, a composition, a proportion of a surface functional group, and the like.

Further, examples of the process including flow processing include a purification (concentration) of protein. More specifically, examples of the process include a process including flow processing of supplying a buffer solution containing protein to a column and performing chromatography (hereinafter, may be referred to as a "protein purification process"). Thereby, it is possible to obtain purified protein as a product.

Examples of a quality of the product (that is, purified protein) include a concentration and a purity of the protein itself, concentrations of aggregates, DNAs, and impurities contained in the purified protein, and the like.

Further, specific examples of the process include a process including processing of performing continuous processing on a film while winding the film by using a roll-to-roll transfer method. More specifically, specific examples of the process include a process including processing of applying a layer forming material on a film (hereinafter, may be referred to as a "layer forming process"), and the film on which a layer is formed can be obtained as a product. Further, specific examples of the process include a process including processing of performing plasma processing on a film (hereinafter, may be referred to as a "surface reforming process"), and the film having a reformed surface can be obtained as a product.

Examples of a quality of the product (that is, the film on which a layer is formed or the film having a reformed surface) include an optical property, a surface roughness, a wrinkle, a crystallinity, and the like.

Further, examples of the quality of the film on which a layer is formed include a coating streak, coating unevenness, a layer thickness, and the like.

Details of the processor will be described later.

Acquisition of Information

In at least one piece of processing of the process, the processor acquires at least one piece of information of chemical information or physical information of an object to be processed and a processed object (hereinafter, may be referred to as "specific information") at two points at which elapses of processing times between before the processing and after the processing are different from each other.

For example, in the processing of the process illustrated in FIG. 1, as two points at which elapses of processing times between before the processing and after the processing are different from each other, the following four patterns are considered. It is assumed that processing proceeds in a time order of $a_1$ point→$b_1$ point→$c_1$ point→$d_1$ point.

(1) $a_1$ point before processing and $d_1$ point after processing
(2) $a_1$ point before processing and $b_1$ point or $c_1$ point during processing
(3) $b_1$ point during processing and $c_1$ point during processing
(4) $b_1$ point or $c_1$ point during processing and $d_1$ point after processing One or a plurality of patterns may be used to acquire the specific information. Further, in one pattern, one piece of specific information may be acquired, or a plurality of pieces of specific information may be acquired.

For example, as illustrated in FIG. 2, in a case where the process includes a plurality of pieces of processing, for the two points at which elapses of processing times between before the processing and after the processing are different from each other, the same patterns as the patterns described in FIG. 1 are considered for each of the pieces of processing.

In the object provided for the processing, an object on which the processing is not performed is called as an "object to be processed", and an object on which the processing is performed is called as a "processed object". The processed object may be a product. Further, the starting material may be an object to be processed.

At the points $a_1, a_2, \ldots,$ and $a_n$ before the processing, only the object to be processed exists.

At the $b_1$ point, the $b_2$ point, . . . , and the $b_n$ point during the processing, and the $c_1$ point, the $c_2$ point, . . . , the $c_n$ point during the processing, the object to be processed and the processed object may coexist.

At the $d_1$ point, the $d_2$ point, . . . , and the $d_n$ point after the processing, the processed object exists. Depending on a degree of progress of the processing, the object to be processed may remain.

Examples of the chemical information include a spectroscopic spectrum (for example, an infrared spectroscopic spectrum, a Raman spectroscopic spectrum, a nuclear magnetic resonance spectrum, and the like), a pH concentration, and the like.

Examples of the physical information include a degree of mixing of a plurality of fluids, a conductivity, a temperature, a transmittance, a refractive index, turbidity, an image, a color, a viscosity, a contact angle, a tension, a state quantity of a flow field, and the like.

Figure 3:
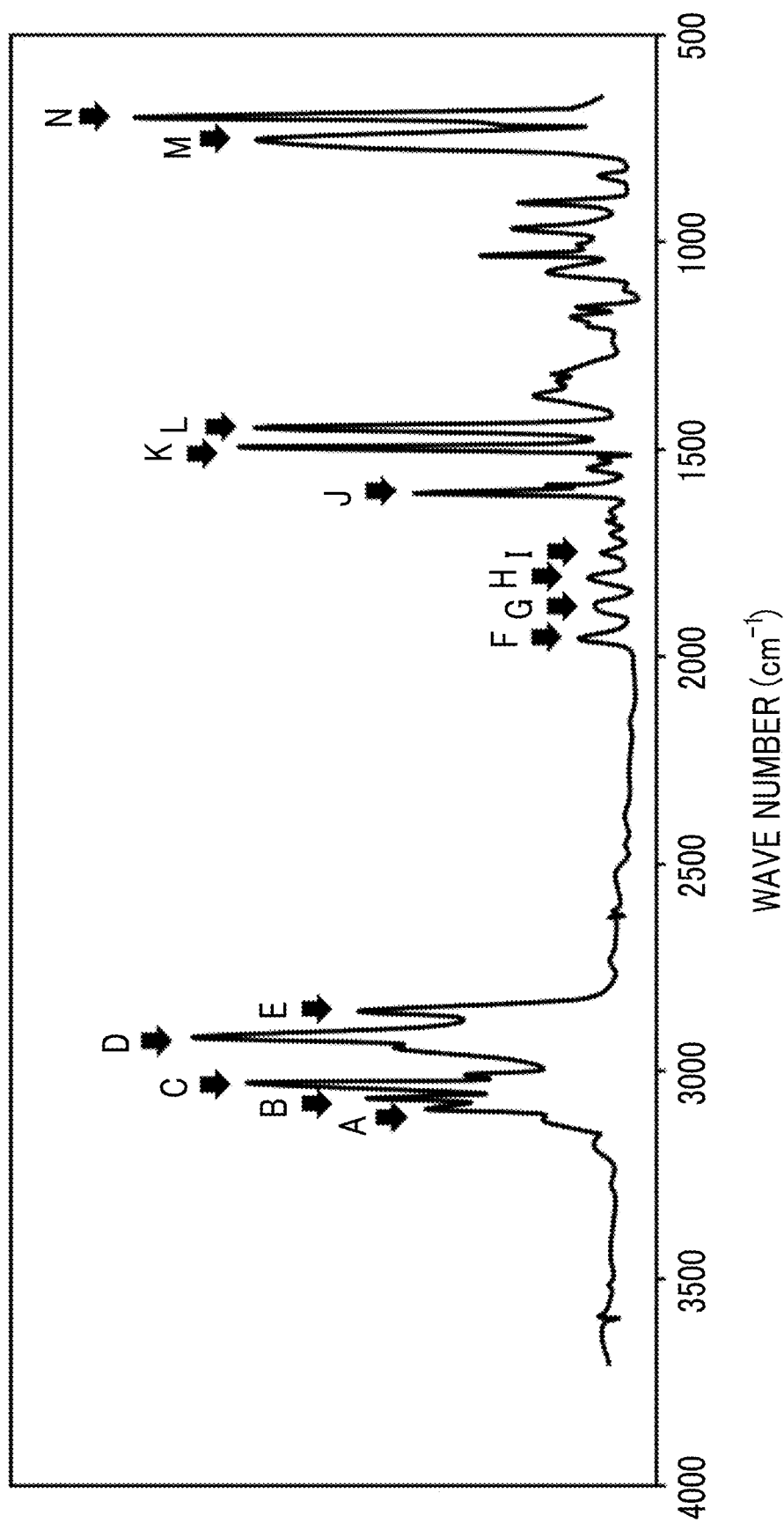
FIG. 3 is a diagram illustrating an example of an infrared spectroscopic spectrum.

The chemical information and the physical information may be acquired by an actual measurement or by a simulation. For example, a spectroscopic spectrum as the chemical information may be acquired by an actual measurement, or may be acquired by a quantum chemical calculation. For example, for polystyrene, an infrared spectroscopic spectrum as illustrated in FIG. 3 may be obtained. Further, examples of the physical information obtained by a simulation include a state quantity of a flow field to be described later.

The processor may acquire, in the acquisition of the information, a spectroscopic spectrum as the chemical information in the at least one piece of processing of the process. The spectroscopic spectrum may be acquired by near-infrared spectroscopic analysis, Fourier transform infrared spectroscopic analysis, Raman spectroscopic analysis, nuclear magnetic resonance spectroscopic analysis, or the like.

In a case where at least one piece of processing of the process is flow processing using a flow path, the processor may acquire, in the acquisition of the information, a state quantity of a flow field as the physical information of the flow processing. The "state quantity of the flow field" is an index illustrating a state of a flow field regardless of a property of a material inside the flow field.

Examples of the state quantity of the flow field include a mixed state (for example, a mixing ratio, an element ratio, uniformity), a flow velocity distribution, a retention time distribution, a Reynolds number, turbulent energy, a temperature distribution, a pressure distribution, and the like.

The processor may acquire, in the acquisition of the information, the state quantity of the flow field by a computational fluid dynamics analysis.

In a case where the flow processing is processing of mixing a plurality of fluids, the state quantity of the flow field may be a mixing ratio of the fluids that is calculated based on the computational fluid dynamics analysis.

Here, the "mixing ratio" means a degree of mixing of the plurality of fluids on a volume basis. By the computational fluid dynamics analysis, the mixed state of the plurality of fluids is simulated, and a region in which each fluid exists without mixing and a region in which at least two fluids are mixed (mixed region) are imaged. A ratio of an area of the mixed region with respect to an area of the entire region (that is, the total area) is defined as a mixing ratio.

Figure 4:
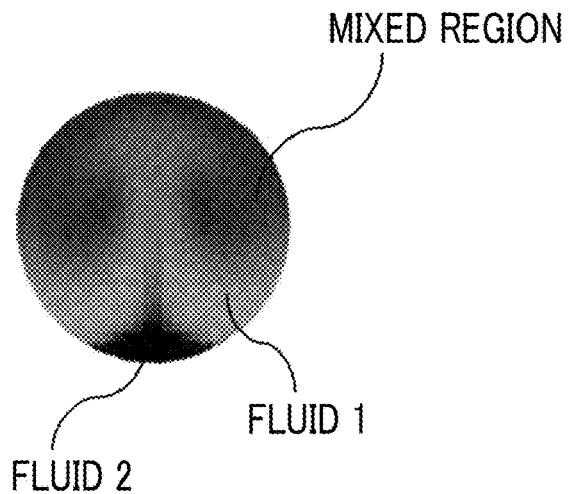
FIG. 4 is a diagram illustrating an example of a mixed state of a fluid obtained by a computational fluid dynamics analysis.

For example, for a mixing ratio of two fluids (fluid 1 and fluid 2), by the computational fluid dynamics analysis, the mixed state of these fluids is simulated, and a region in which the two fluids exist without mixing and a region in which the two fluids are mixed (mixed region) are imaged. By displaying the fluid 1 in white, displaying the fluid 2 in black, and displaying the region in which the two fluids are mixed (mixed region) in gray, for example, as illustrated in FIG. 4, the mixed state is imaged. The mixing ratio can be obtained from an area of the mixed region with respect to an area of the entire region.

Figure 5:
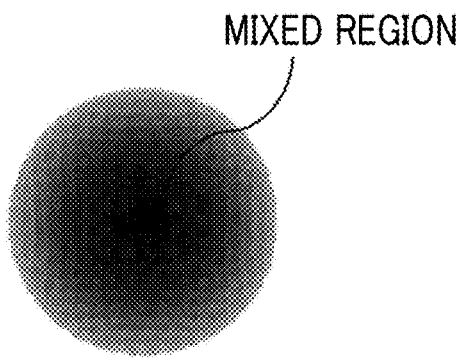
FIG. 5 is a diagram illustrating an example of a mixed state of a fluid obtained by a computational fluid dynamics analysis.

Further, by simulating a state where mixing is further progressed than in the mixed state illustrated in FIG. 4, for example, a mixed state as illustrated in FIG. 5 can be imaged. In the mixed state illustrated in FIG. 5, the fluid 1 and the fluid 2 are completely mixed, and the mixing ratio is 1.

The computational fluid dynamics analysis may be performed using general simulation software (open source, commercial software, or the like). Examples of an analysis condition include a flow velocity of a fluid, a flow rate of a fluid, a pressure of a fluid (defined as a boundary condition at an inlet portion and an outlet portion of an analysis region), a concentration of a fluid (defined as a concentration at an inlet portion of an analysis region in a case of calculating mixing or the like of fluids), a shape of an analysis region (for example, corresponding to a diameter and a length of a tube through which a fluid flows), physical property information of a fluid (a viscosity, a kinematic viscosity coefficient, a density, a diffusion coefficient, and the like), a pressure of a pump, and the like.

Acquisition of Calculation Value

The processor acquires a calculation value of a difference (hereinafter, may be simply referred to as a "difference") between the numerical values at the two points (hereinafter, may be referred to as "information values") obtained from the information. Hereinafter, the calculation value of the difference may be simply referred to as a "calculation value".

Examples of the information value include an intensity and an integrated intensity obtained from a spectroscopic spectrum (for example, a peak intensity and an integrated intensity at a peak), chromaticity, an analysis value of an image (brightness or the like), a physical property value of the chemical information and the physical information described above, and the like.

The processor may acquire, in the acquisition of the calculation value, the calculation value of an intensity at a wave number or the calculation value of an integrated intensity in a wave number region, the wave number and the wave number region being a characteristic wave number and a characteristic wave number region in the spectral spectrum changed by the at least one piece of processing.

In this aspect, the processor may determine the wave number or the wave number region based on a quantum chemical calculation. Thereby, it is possible to determine a desired wave number.

Further, in a case where the wave number or the wave number region is determined based on a quantum chemical calculation, it is easy to extract a wave number or a wave number region that is considered to be involved in a reaction. Therefore, it is possible to prevent the wave number or the wave number region correlated with the objective variable from being considered in the machine learning model even though a contribution to a reaction is low (or no contribution). Thereby, it is possible to predict the quality with higher accuracy.

In an aspect of acquiring, for a characteristic wave number or a characteristic wave number region, a calculation value of an intensity at the wave number or a calculation value of an integrated intensity in the wave number region as described above, by sparse modeling, a wave number having a high contribution to prediction accuracy may be extracted from a plurality of wave numbers.

In the aspect, the characteristic wave number or the characteristic wave number region may include a wave number or a wave number region derived from a by-product. In a case where generation of a by-product and a generation amount of the by-product correspond to a characteristic chemical reaction, by selecting a wave number or a wave number region derived from the by-product as a characteristic wave number or a characteristic wave number region, it is possible to predict the quality with higher accuracy.

For example, in an infrared spectroscopic spectrum of polystyrene illustrated in FIG. 3, a characteristic wave number can be determined by a quantum chemical calculation, and peak intensities of a peak A to a peak N corresponding to the determined wave number can be obtained. A peak A to a peak C are derived from a C—H expansion and contraction of an aromatic ring, and a peak D and a peak E are derived from a C—H expansion and contraction of an aliphatic. A peak F to a peak I are derived from a monosubstituted product of an aromatic ring, and a peak J and a peak K are derived from a C=C expansion and contraction of an aromatic ring. A peak L is derived from a C—H variation angle, a peak M is derived from C—H out-of-plane variation angle, and a peak N is derived from a variation angle of an aromatic ring. Further, each peak may also include peak elements derived from a by-product and an unreacted reactant in addition to polystyrene as a product.

Prediction of Quality

The processor sets the difference as an explanatory variable, sets the quality of the product as an objective variable, and predicts the quality of the product based on the calculation value by using a trained model obtained by performing machine learning based on a known data set of the explanatory variable and the objective variable.

Details of the trained model will be described later.

Acquisition of Condition Value

The processor acquires a condition value of a processing condition for the at least one piece of processing of the process (hereinafter, may be simply referred to as "acquisition of a condition value"). In this aspect, the explanatory variable includes a processing condition in addition to the difference, the processor predicts the quality of the product based on the calculation value and the condition value in the prediction of the quality. Thereby, it is possible to predict the quality with higher accuracy.

In a case of the flow processing, examples of the condition value include a flow velocity of a fluid, a concentration of a fluid, a diameter and a length of a tube through which a fluid flows, a reaction temperature, a viscosity of a fluid, a pressure of a pump, and the like.

The condition value may be an actually measured value or a set value.

Example of Polymer Synthesis Process

An example of the polymer synthesis process will be described. In the first flow processing of mixing a plurality of raw materials, at the $a_1$ point before the processing, a plurality of raw materials (objects to be processed) exist.

At the $b_1$ point and the $c_1$ point during the first flow processing, some of the plurality of raw materials are mixed. That is, unmixed raw materials (objects to be processed) and mixed raw materials (processed objects) coexist. A mixing ratio may differ at the $b_1$ point and the $c_1$ point.

At the $d_1$ point after the first flow processing, mixed raw materials (processed objects) exist.

For example, the mixing ratio may be acquired at the $b_1$ point during the first flow processing and the $c_1$ point during the first flow processing (acquisition of information). The calculation value of the difference between the numerical values at the two points is acquired from the numerical values obtained from the mixing ratio, for example, the mixing ratio itself (acquisition of a calculation value).

In the second flow processing of heating and polymerizing the mixed raw materials, at the $a_2$ point before the processing, the mixed raw materials (objects to be processed) exist.

At the $b_2$ point during the second flow processing and the $c_2$ point during the second flow processing, a part of the mixed raw materials (objects to be processed) is polymerized, and thus polymer (the processed object, the product) is generated. At the $b_2$ point and the $c_2$ point, a degree of progress of polymerization may differ.

At the $d_2$ point after the second flow processing, polymer (processed object, the product) exists.

For example, at the $a_2$ point before the second flow processing and the $d_2$ point after the second flow processing, an infrared spectroscopic spectrum may be acquired (acquisition of information). The calculation value of the difference between the numerical values at the two points is acquired from the numerical values obtained from the infrared spectroscopic spectrum, for example, the integrated intensities at the peaks (acquisition of calculation value).

For example, a number-average molecular weight may be selected as the quality of the product (polymer).

The processor sets at least one of the difference obtained from the mixing ratio or the difference obtained from the integrated intensities at the peaks as the explanatory variable, sets the number-average molecular weight as the objective variable, and configures a trained model by performing machine learning based on known data sets of the explanatory variable and the objective variable. By using the trained model, the processor predicts the number-average molecular weight of the polymer based on the calculation value (prediction of quality).

Examples of the processing condition of the first flow processing include a flow velocity of the raw material, a concentration of the raw material, and a diameter and a length of a tube through which a fluid flows, and examples of the processing condition of the second flow processing include a reaction temperature. The value may be acquired as a condition value of the processing condition (acquisition of a condition value).

In a case where the condition value of the processing condition is acquired, the processor sets at least one processing condition of the difference as the explanatory variable, sets the number-average molecular weight as the objective variable, and configures a trained model by performing machine learning based on known data sets of the explanatory variable and the objective variable. By using the trained model, the processor predicts the number-average molecular weight of the polymer based on the calculation value and the condition value (prediction of quality).

Example of Protein Purification Process

An example of a protein purification process will be described. In the flow processing of supplying a buffer solution containing protein to a column and performing chromatography, at the $a_1$ point before the processing, an unprocessed buffer solution (object to be processed) exists.

At the $b_1$ point during the flow processing and the $c_1$ point during the flow processing, impurities are separated from a part of the buffer solution.

At the $d_1$ point after the flow processing, the buffer solution (processed object) containing purified protein with few impurities exists.

For example, at the $a_1$ point before the flow processing and the $d_1$ point after the flow processing, a spectroscopic spectrum may be acquired (acquisition of information). The calculation value of the difference between the numerical values at the two points is acquired from the numerical values obtained from the spectroscopic spectrum, for example, the integrated intensities at the peaks (acquisition of calculation value).

For example, as the quality of the product (purified protein), a purity may be selected.

The processor sets the difference as the explanatory variable, sets the purity as the objective variable, and configures a trained model by performing machine learning based on known data sets of the explanatory variable and the objective variable. By using the trained model, the processor predicts the purity of the purified protein based on the calculation value (prediction of a quality).

Examples of the processing condition of the flow processing include a pressure of a pump. The value may be acquired as a condition value of the processing condition (acquisition of a condition value).

In a case where the condition value of the processing condition is acquired, the processor sets the difference and the processing condition as the explanatory variables, sets the purity as the objective variable, and configures a trained model by performing machine learning based on known data sets of the explanatory variables and the objective variable. By using the trained model, the processor predicts the purity of the purified protein based on the calculation value and the condition value (prediction of a quality).

Layer Forming Process

An example of a layer forming process will be described. In processing of applying a layer forming material on a film, at the $a_1$ point before the processing, a film (an object to be processed) on which the layer forming material is not applied exists.

At the $b_1$ point during the processing and the $c_1$ point during the processing, a layer is formed on a part of the film.

At the $d_1$ point after the processing, a film (processed object) on which a layer is wholly formed exists.

For example, transmittance may be acquired at the $b_1$ point during the processing and the $c_1$ point during the processing (acquisition of information). The calculation value of the difference between the numerical values at the two points is acquired from the numerical values obtained from the transmittance, for example, the transmittance itself (acquisition of a calculation value). In this case, for example, as the quality of the product (the film on which a layer is formed), a thickness of the layer may be selected.

The processor sets the difference as the explanatory variable, sets the thickness of the layer as the objective variable, and configures a trained model by performing machine learning based on known data sets of the explanatory variable and the objective variable. By using the trained model, the processor predicts the thickness of the layer of the film on which the layer is formed based on the calculation value (prediction of a quality).

For example, a tension of the film may be acquired at the $b_1$ point during the processing and the $c_1$ point during the processing (acquisition of information). The calculation value of the difference between the numerical values at the two points is acquired from the numerical values obtained from the tension, for example, the tension itself (acquisition of a calculation value). In this case, for example, as the quality of the product (the film on which a layer is formed), the presence or absence of a wrinkle may be selected.

The processor sets the difference as the explanatory variable, sets the presence or absence of a wrinkle as the objective variable, and configures a trained model by performing machine learning based on known data sets of the explanatory variable and the objective variable. By using the trained model, the processor predicts the presence or absence of a wrinkle of the film on which the layer is formed based on the calculation value (prediction of a quality).

Surface Reforming Process

An example of a surface reforming process will be described. In processing of performing plasma processing on a film, at the $a_1$ point before the processing, a film (an object to be processed) on which plasma processing is not performed exists.

At the $b_1$ point during the processing and the $c_1$ point during the processing, plasma processing is performed on a part of the film.

At the $d_1$ point after the processing, a film (processed object) on which plasma processing is wholly performed exists.

For example, a temperature may be acquired at the $b_1$ point during the processing and the $c_1$ point during the processing (acquisition of information). The calculation value of the difference between the numerical values at the two points is acquired from the numerical values obtained from the temperature, for example, the temperature itself (acquisition of a calculation value).

For example, as the quality of the product (the film on which plasma processing is performed), a contact angle may be selected.

The processor sets the difference as the explanatory variable, sets the contact angle as the objective variable, and configures a trained model by performing machine learning based on known data sets of the explanatory variable and the objective variable. By using the trained model, the processor predicts the contact angle of the film on which plasma processing is performed based on the calculation value (prediction of a quality).

Hereinafter, an information processing apparatus according to the present disclosure will be described in more detail with reference to a first embodiment and a second embodiment by taking a polymer synthesis process as an example.

First Embodiment

Figure 6:
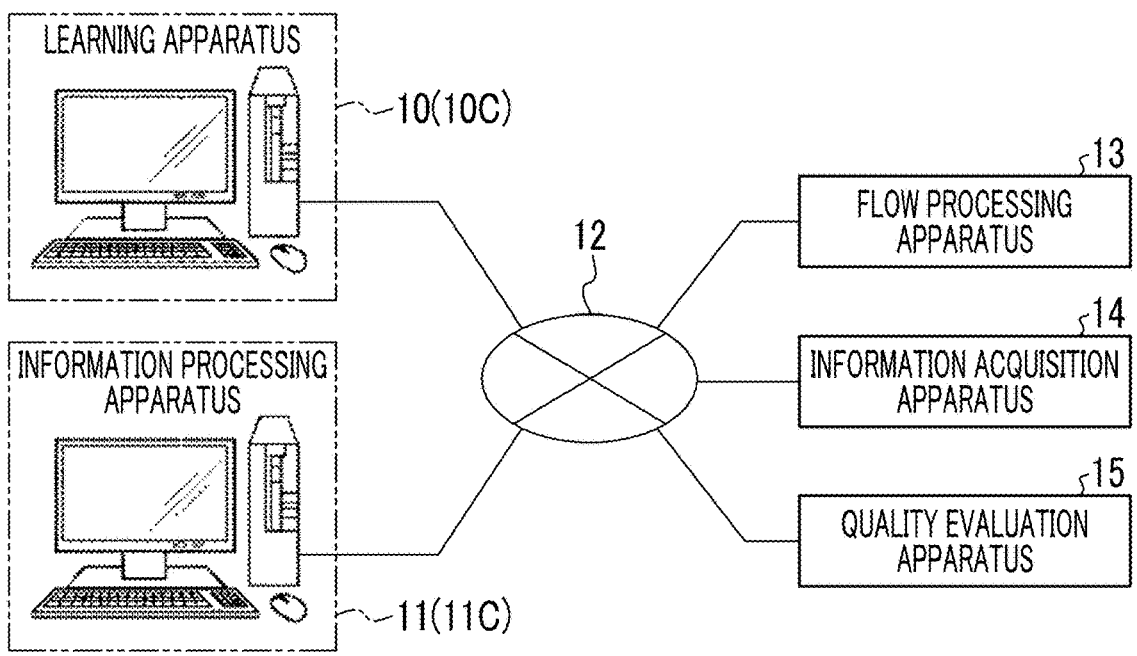
FIG. 6 is a diagram illustrating an information processing apparatus, a learning apparatus, a flow processing apparatus, an information acquisition apparatus, and a quality evaluation apparatus.

In FIG. 6, the information processing apparatus 11 and the learning apparatus 10 configuring a trained model are connected to each other so as to communicate with each other via a network 12. The learning apparatus 10 and the information processing apparatus 11 are, for example, desktop personal computers. The network 12 is, for example, a local area network (LAN) or a wide area network (WAN) such as the Internet or a public communication network. A flow processing apparatus 13, an information acquisition apparatus 14, and a quality evaluation apparatus 15 are also connected to the network 12.

Figure 7:
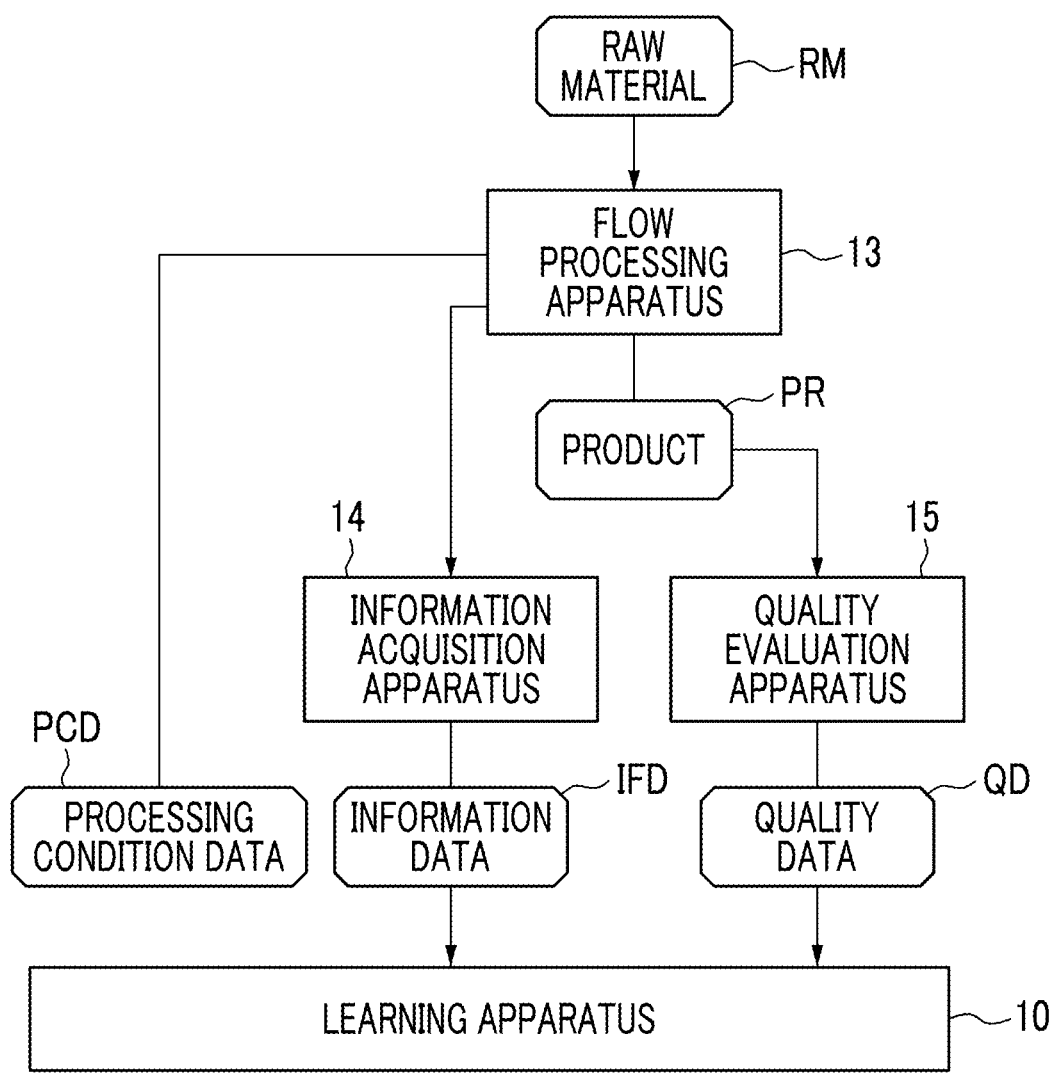
FIG. 7 is a diagram illustrating an outline of processing in the flow processing apparatus, the information acquisition apparatus, and the quality evaluation apparatus.

In FIG. 7, the flow processing apparatus 13 produces a product PR from a raw material RM according to processing condition data PCD by a process including the flow processing. In at least one piece of processing of the process, the information acquisition apparatus 14 acquires specific information at two points at which elapses of processing times between before the processing and after the processing are different from each other, and outputs acquired information data IFD. The quality evaluation apparatus 15 evaluates a quality of the product PR, and outputs quality data QD as an evaluation result. The information data IFD is transmitted from the information acquisition apparatus 14 to the learning apparatus 10, and the quality data QD is transmitted from the quality evaluation apparatus 15 to the learning apparatus 10.

Figure 8:
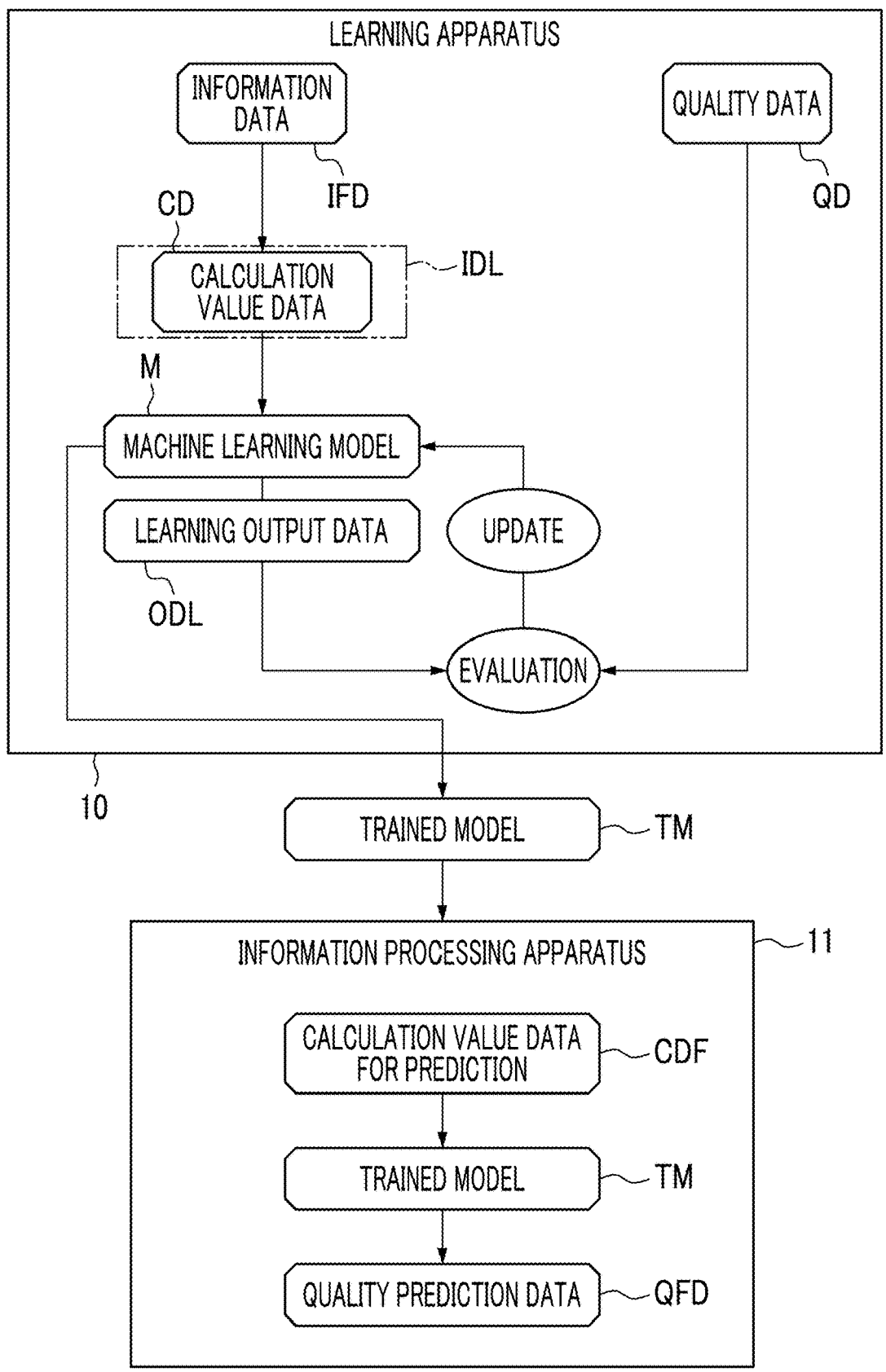
FIG. 8 is a diagram illustrating an outline of processing in the information processing apparatus and the learning apparatus.
Figure 9:
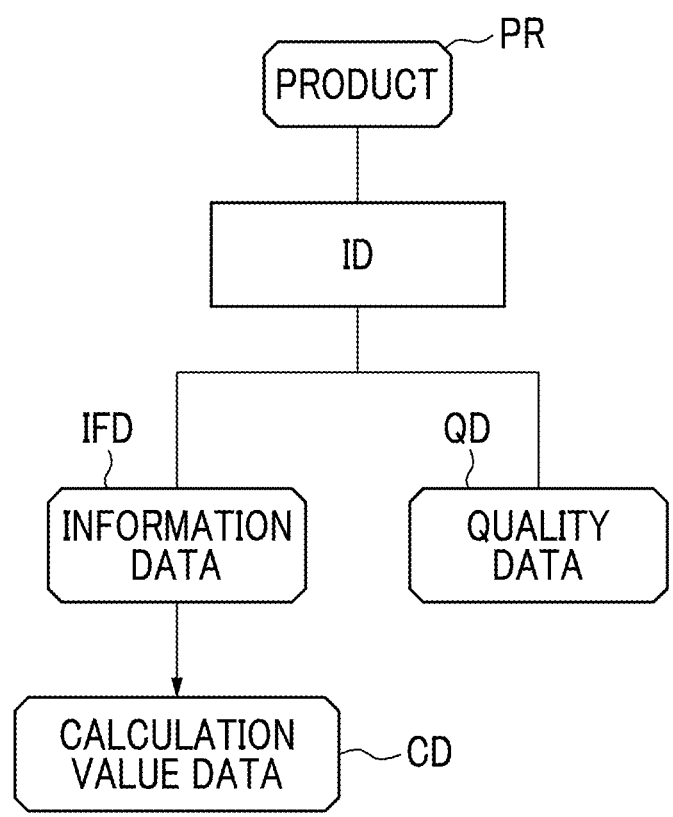
FIG. 9 is a diagram illustrating that information data, calculation value data, and quality data are associated with a common ID.

In FIG. 8, the learning apparatus 10 acquires the information data IFD from the information acquisition apparatus 14 and the quality data QD from the quality evaluation apparatus 15. The learning apparatus 10 derives calculation value data CD of a difference from the information data IFD (hereinafter, abbreviated as calculation value data). It is assumed that the calculation value data CD is the learning input data IDL. As illustrated in FIG. 9, the information data IFD, the calculation value data CD derived from the information data IFD, and the quality data QD are associated with common identification data (ID) which is assigned to one product PR. The calculation value data CD and the quality data QD are included in a known data set.

The learning apparatus 10 includes a machine learning model M. The machine learning model M is a model for predicting a quality of the product PR. The machine learning model M outputs learning output data ODL according to the learning input data IDL.

As the machine learning model M, there are machine learning models using linear regression, Gaussian process regression, support vector regression, decision tree, regression tree, an ensemble method, a bagging method, a boosting method, a gradient boosting method, and the like. Further, there are machine learning models using a simple perceptron, a multi-layer perceptron, a deep neural network, a convolutional neural network, a deep belief network, a recurrent neural network, a stochastic neural network, and the like. Which machine learning model M is used among the above-described models is not particularly limited, and a machine learning model M using any method may be selected.

As an ensemble method, there is random forest. As well known, random forest is a method of improving accuracy of prediction by creating a plurality of decision tree groups with low correlation using randomly-sampled learning data and randomly-selected explanatory variables and integrating and averaging prediction results by the decision tree groups. In this case, control parameters of the machine learning model M include the number of explanatory variables to be selected and the number of branches of the decision trees.

Since the deep neural network has the relatively large number of control parameters, flexible combinations may be made. For this reason, the deep neural network can exhibit high prediction performance for various data structures. The control parameters include the number of layers of the network and the number of nodes of the network, a type of an activated function, a dropout ratio, a mini-batch size, the number of epochs, a learning rate, and the like.

The machine learning model M includes a plurality of execution frameworks, and an execution framework may be appropriately selected from the execution frameworks. For example, an execution framework may be selected from Tensorflow, Cognitive Toolkit (CNTK), Theano, Caffe, mxnet, Keras, PyTorch, Chainer, Scikit-learn, Caret, MATLAB, and the like.

The quality data QD is data for matching the learning output data ODL with an answer. As an accuracy of prediction of the machine learning model M is higher, a difference between the quality data QD and the learning output data ODL is smaller. Therefore, the learning apparatus 10 evaluates an accuracy of prediction of the machine learning model M by comparing the learning output data ODL with the quality data QD having the same ID as the learning input data IDL. The machine learning model M is updated according to the evaluation result. The learning apparatus 10 inputs the learning input data IDL to the machine learning model M, outputs the learning output data ODL from the machine learning model M, evaluates an accuracy of prediction of the machine learning model M, and updates the machine learning model M, while changing the learning input data IDL and the quality data QD. The series of processing is repeated until an accuracy of prediction of the machine learning model M reaches a preset level. The learning apparatus 10 transmits, to the information processing apparatus 11, the machine learning model M of which an accuracy of prediction reaches a preset level, as a trained model TM to be used for actual operation.

The information processing apparatus 11 receives the trained model TM from the learning apparatus 10. The information processing apparatus 11 inputs, to the trained model TM, the calculation value data for prediction CDF, which is calculation value data of the product PR of which a quality is unknown. The calculation value data for prediction CDF is data derived from the information data for prediction IFDF, which is information data IFD of the product PR of which a quality is unknown, similar to the calculation value data CD. The trained model TM outputs quality prediction data QFD according to the calculation value data for prediction CDF.

In the first embodiment, the flow processing apparatus 13 performs an anionic polymerization reaction of polystyrene as a product PR by a process including two pieces of flow processing (first flow processing and second flow processing) using a flow path.

The first flow processing is processing of mixing a first raw material RM1 (a solution obtained by dissolving polystyryl lithium in a solvent) and a second raw material RM2 (a methanol aqueous solution), and a mixture of the first raw material RM1 and the second raw material RM2 (hereinafter, may be referred to as a "raw material mixture") is obtained. The second flow processing is processing of performing an anionic polymerization reaction on the raw material mixture, and polystyrene as a product PR is obtained.

The polystyryl lithium produces polystyrene as a product PR by an anionic polymerization reaction. As the solvent, tetrahydrofuran is used. In addition, a small amount of toluene and a small amount of hexane are mixed in the solution. A raw material for the flow processing may be a mixture of a reactant such as polystyryl lithium and another substance, such as the first raw material RM1, or may be made of only a reactant.

Further, methanol is used as a terminator for an anionic polymerization reaction.

Figure 10:
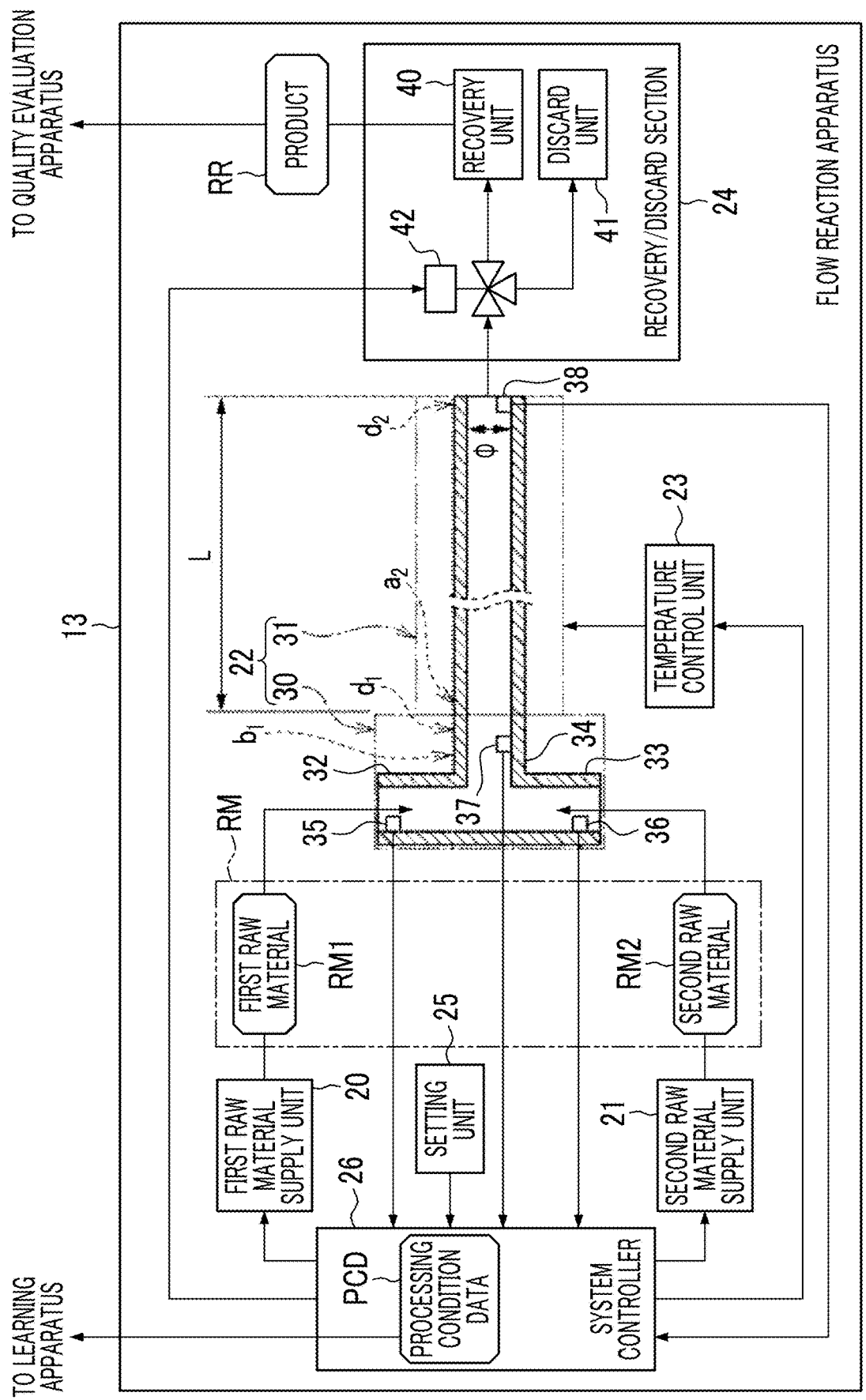
FIG. 10 is a diagram illustrating the flow processing apparatus with a processing section including a T-shaped junction portion.

In FIG. 10, the flow processing apparatus 13 includes a first raw material supply unit 20, a second raw material supply unit 21, a processing section 22, a temperature control unit 23, a recovery/discard section 24, a setting unit 25, a system controller 26, and the like.

The first raw material supply unit 20 is connected to an upstream end of the processing section 22 by a pipe (not illustrated). The first raw material supply unit 20 supplies a first raw material RM1 to the processing section 22. The first raw material supply unit 20 includes a pump for transporting the first raw material RM1 to the processing section 22. By controlling a rotation speed of the pump, a flow rate of the first raw material RM1 which is transported from the first raw material supply unit 20 to the processing section 22 is adjusted.

Similar to the first raw material supply unit 20, the second raw material supply unit 21 is connected to the upstream end of the processing section 22 by a pipe (not illustrated). The second raw material supply unit 21 supplies a second raw material RM2 to the processing section 22. Similar to the first raw material supply unit 20, the second raw material supply unit 21 also includes a pump for transporting the second raw material RM2 to the processing section 22. By controlling a rotation speed of the pump, a flow rate of the second raw material RM2 which is transported from the second raw material supply unit 21 to the processing section 22 is adjusted.

The processing section 22 is a section for performing the first flow processing (mixing processing) and the second flow processing (processing for performing an anionic polymerization reaction). The processing section 22 includes a junction portion 30 and a reaction portion 31. The first flow processing is performed in the junction portion 30, and the second flow processing is performed in the reaction portion 31.

The junction portion 30 includes a first pipe portion 32, a second pipe portion 33, and a third pipe portion 34. The first pipe portion 32 and the second pipe portion 33 are connected in a straight line, and the third pipe portion 34 intersects with the first pipe portion 32 and the second pipe portion 33 at a right angle. That is, the junction portion 30 has a T-shape.

The first pipe portion 32 is connected to the first raw material supply unit 20, and the second pipe portion 33 is connected to the second raw material supply unit 21. Further, the third pipe portion 34 is connected to the reaction portion 31. The first raw material RM1 is supplied from the first raw material supply unit 20 to the first pipe portion 32, and the second raw material RM2 is supplied from the second raw material supply unit 21 to the second pipe portion 33. The first raw material RM1 and the second raw material RM2 are mixed in the third pipe portion 34, and are transported to the reaction portion 31 in a mixed state.

A first flow velocity sensor 35 that detects a flow velocity of the first raw material RM1 passing through the first pipe portion 32 is provided in the first pipe portion 32. In addition, a second flow velocity sensor 36 that detects a flow velocity of the second raw material RM2 passing through the second pipe portion 33 is provided in the second pipe portion 33. In addition, a third flow velocity sensor 37 that detects a flow velocity of a raw material mixture passing through the third pipe portion 34 is provided in the third pipe portion 34.

The reaction portion 31 is an elongated pipe obtained by connecting a plurality of linear-shaped pipes having the same inner diameter in a straight line. A length L of the reaction portion 31 may be changed by changing the number of linear-shaped pipes to be connected and/or lengths of the linear-shaped pipes. Further, the inner diameter 4) of the reaction portion 31 may be changed by changing the inner diameter of the linear-shaped pipe to be connected.

The inside of the reaction portion 31 is a flow path through which the raw material mixture flows, and is a place where the second flow processing is performed. In a case where the raw material mixture passes through the reaction portion 31, an anionic polymerization reaction is promoted, and thus a polystyrene solution is obtained. The second flow processing is slightly promoted in the third pipe portion 34 of the junction portion 30. On the other hand, a length of the third pipe portion 34 is very shorter than a length L of the reaction portion 31. For this reason, the length of the third pipe portion 34 is ignored, and the length L of the reaction portion 31 is regarded as a length of a reaction path, which is a length of a portion at which the second flow processing is performed. Similarly, the inner diameter 4) of the reaction portion 31 is regarded as a diameter of the reaction path, which is a diameter of a portion at which the second flow processing is performed.

The temperature control unit 23 includes a heater and/or a cooler, and controls a temperature inside the reaction portion 31 (hereinafter, referred to as a reaction temperature). A temperature sensor 38 for detecting the reaction temperature is provided at a downstream end of the reaction portion 31.

The recovery/discard section 24 is a section for recovering polystyrene which is the product PR and discarding a waste in which a reaction is failed. The recovery/discard section 24 includes a recovery unit 40 and a discard unit 41. The recovery unit 40 and the discard unit 41 are connected to the downstream end of the reaction portion 31 by a three-way valve 42. By using the three-way valve 42, switching between a recovery line that connects the reaction portion 31 and the recovery unit 40 and a discard line that connects the reaction portion 31 and the discard unit 41 can be performed.

The recovery unit 40 precipitates polystyrene from the polystyrene solution. The recovery unit 40 collects the precipitated polystyrene by filtering the solution. The collected polystyrene is dried. More specifically, the recovery unit 40 includes a container with a stirrer, and precipitates polystyrene by filling the container with methanol and mixing the polystyrene solution into the stirred methanol. Further, the recovery unit 40 includes a constant-temperature tank with a depressurization function, and dries the methanol by heating the inside of the constant-temperature tank in a depressurization state.

The discard unit 41 is a tank for storing a waste. Here, the waste is transported from the reaction portion 31 in a case where the flow velocity of the first raw material RM1, the flow velocity of the second raw material RM2, the flow velocity of the raw material mixture, the reaction temperature, or the like is disturbed for some reason and, as a result, production cannot be performed under originally-predetermined processing conditions.

The setting unit 25 receives setting of processing conditions of the product PR by an operator of the flow processing apparatus 13. The processing conditions received by the setting unit 25 are registered in the system controller 26, as the processing condition data PCD.

The system controller 26 overall controls operations of the entire flow processing apparatus 13. The system controller 26 is connected to the first raw material supply unit 20, the second raw material supply unit 21, the temperature control unit 23, the first flow velocity sensor 35, the second flow velocity sensor 36, the third flow velocity sensor 37, the temperature sensor 38, and the three-way valve 42.

The system controller 26 adjusts the flow rate of the first raw material RM1 by controlling the rotation speed of the pump of the first raw material supply unit 20 according to the flow velocity of the first raw material RM1 that is detected by the first flow velocity sensor 35. Similarly, the system controller 26 adjusts the flow rate of the second raw material RM2 by controlling the rotation speed of the pump of the second raw material supply unit 21 according to the flow velocity of the second raw material RM2 that is detected by the second flow velocity sensor 36. In addition, the system controller 26 drives the temperature control unit 23 according to the reaction temperature detected by the temperature sensor 38. Further, the system controller 26 performs switching between the recovery line and the discard line by controlling the three-way valve 42.

Examples of the processing condition data PCD include a concentration (unit: mol/l) and a flow velocity (unit: ml/min) of the first raw material RM1, a concentration (unit: mol/l) and a flow velocity (unit: ml/min) of the second raw material RM2, a diameter $\Phi$ (unit: mm) of the reaction path, a length L (unit: m) of the reaction path, and a reaction temperature (unit: ° C.).

The system controller 26 adjusts the flow rate of the first raw material RM1 by controlling the rotation speed of the pump of the first raw material supply unit 20 such that, for example, the flow velocity of the first raw material RM1 detected by the first flow velocity sensor 35 matches with the flow velocity of the first raw material RM1 registered in the processing condition data PCD. Similarly, for example, the system controller 26 adjusts the flow rate of the second raw material RM2 by controlling the rotation speed of the pump of the second raw material supply unit 21 such that the flow velocity of the second raw material RM2 detected by the second flow velocity sensor 36 matches with the flow velocity of the second raw material RM2 registered in the processing condition data PCD.

Further, the system controller 26 drives the temperature control unit 23 such that the reaction temperature detected by the temperature sensor 38 matches with a reaction temperature registered in the processing condition data PCD.

In a case where a deviation between each value detected by each of the first flow velocity sensor 35, the second flow velocity sensor 36, and the temperature sensor 38 (further, a first flow velocity sensor 51, a second flow velocity sensor 52, and a third temperature sensor 53, which will be described later) and each value registered in the processing condition data PCD exceeds a preset range, the system controller 26 controls the three-way valve 42 to perform switching to the discard line and guide the waste to the discard unit 41. In a case where the reaction fails and the waste is generated, of course, the information data IFD and the quality data QD are not output. Therefore, in a case where the waste is generated, the processing condition data PCD is discarded without being transmitted to the learning apparatus 10.

In at least one piece of processing of the first flow processing or the second flow processing, the information acquisition apparatus 14 acquires specific information (that is, at least one piece of information of chemical information or physical information of an object to be processed and a processed object) at two points at which elapses of processing times between before the processing and after the processing are different from each other, and outputs the acquired information data IFD.

Further, for example, in the first flow processing, the information acquisition apparatus 14 may acquire the specific information at two points at which elapses of processing times between before the processing and after the processing are different from each other, that is, a $b_1$ point of the first pipe portion 32 and a $d_1$ point of the third pipe portion 34 that are illustrated in FIG. 10. The specific information may be, for example, a state quantity (physical information) of a flow field.

For example, in the second flow processing, the information acquisition apparatus 14 may acquire the specific information at two points at which elapses of processing times between before the processing and after the processing are different from each other, that is, an $a_2$ point and a $d_2$ point of the reaction portion 31 illustrated in FIG. 10. The specific information may be, for example, an infrared spectroscopic spectrum (chemical information).

For example, the quality evaluation apparatus 15 may output a number-average molecular weight of the product PR as the quality data QD.

Figure 11:
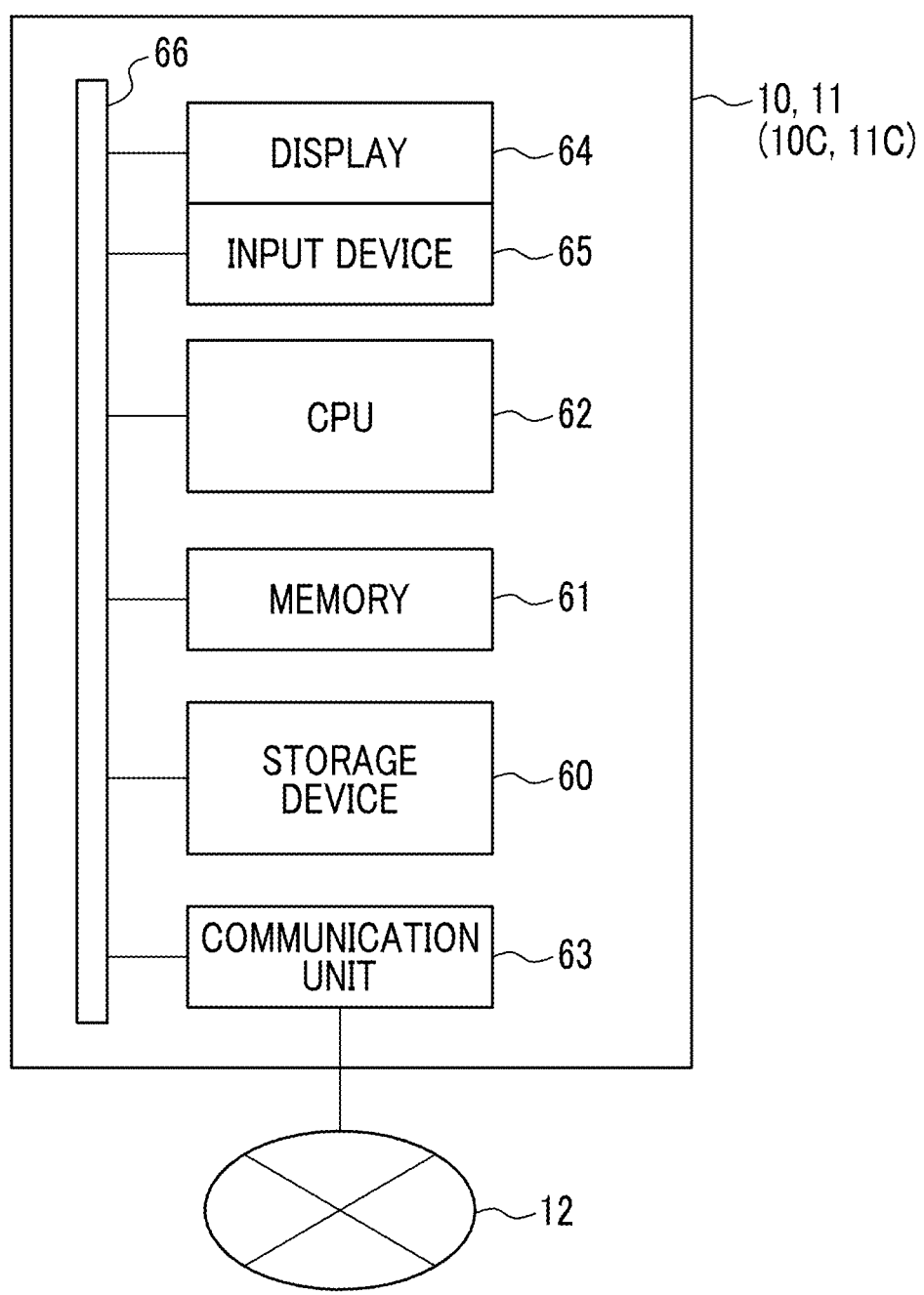
FIG. 11 is a block diagram illustrating a computer constituting the information processing apparatus and the learning apparatus.

In FIG. 11, the computers including the learning apparatus 10 and the information processing apparatus 11 (hereinafter, may be collectively referred to as "information processing apparatus or the like") have the same basic configuration, and each of the computers includes a storage device 60, a memory 61, a central processing unit (CPU, processor) 62, a communication unit 63, a display 64, and an input device 65. The components are connected to each other via a bus line 66.

The storage device 60 is a hard disk drive that is built in the computer including the information processing apparatus 11 or the like or is connected via a cable or a network. Alternatively, the storage device 60 is a disk array in which a plurality of hard disk drives are connected in series. The storage device 60 stores a control program such as an operating system, various application programs, and various data associated with the programs. A solid state drive may be used instead of or in addition to the hard disk drive.

The memory 61 is a work memory which is necessary to execute processing by the CPU 62. The CPU 62 loads the program stored in the storage device 60 into the memory 61, and collectively controls each unit of the computer by executing processing according to the program.

The communication unit 63 is a network interface that controls transmission of various information via the network 12. The display 64 displays various screens. The computer including the learning apparatus 10 or the like receives an input of an operation instruction from the input device 65 via the various screens. The input device 65 includes a keyboard, a mouse, a touch panel, and the like.

In the following description, in order to distinguish the components, a subscript "A" is attached to each component of the learning apparatus 10, and a subscript "B" is attached to each component of the information processing apparatus 11.

Figure 12:
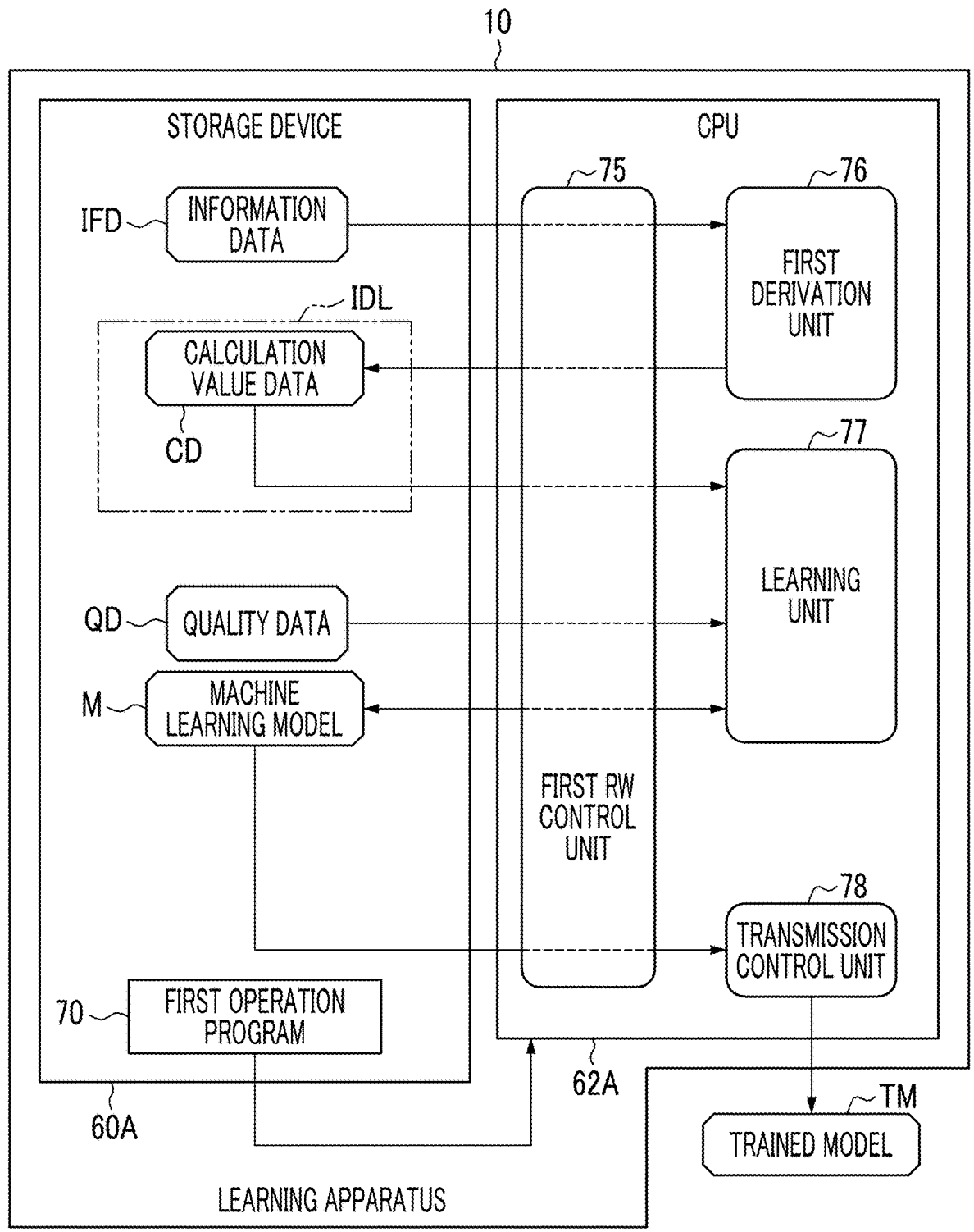
FIG. 12 is a block diagram illustrating a processing unit of a CPU of the learning apparatus.

In FIG. 12, a first operation program 70 is stored in the storage device 60A of the learning apparatus 10. The first operation program 70 is an application program for causing the computer to function as the learning apparatus 10.

The storage device 60A also stores the information data IFD from the information acquisition apparatus 14 and the quality data QD from the quality evaluation apparatus 15. The calculation value data CD derived from the information data IFD and the machine learning model M are also stored. A plurality of sets of the information data IFD, the calculation value data CD, and the quality data QD are stored.

In a case where the first operation program 70 is started, the CPU 62A of the computer including the learning apparatus 10 functions as a first read/write (hereinafter, abbreviated as RW) control unit 75, a first derivation unit 76, a learning unit 77, and a transmission control unit 78, in cooperation with the memory 61 and the like.

The first RW control unit 75 controls reading of various data stored in the storage device 60A and storing of various data in the storage device 60A. The first RW control unit 75 reads the information data IFD from the storage device 60A, and outputs the information data IFD to the first derivation unit 76. Further, the first RW control unit 75 stores the calculation value data CD from the first derivation unit 76 in the storage device 60A. In a case where the information data IFD is a spectroscopic spectrum, the first derivation unit 76 may determine a wave number of a peak or a wave number region of peaks based on a quantum chemical calculation. At that time, a wave number having a high contribution to the prediction accuracy may be extracted from a plurality of wave numbers by sparse modeling.

The first RW control unit 75 reads the calculation value data CD and the quality data QD from the storage device 60A, and outputs the read data to the learning unit 77. In addition, the first RW control unit 75 reads the machine learning model M from the storage device 60A, and outputs the machine learning model M to any of the learning unit 77 and the transmission control unit 78. Further, the first RW control unit 75 stores the machine learning model M from the learning unit 77 in the storage device 60A.

The first derivation unit 76 receives the information data IFD from the first RW control unit 75. The first derivation unit 76 derives the calculation value data CD from the information data IFD. The first derivation unit 76 assigns the same ID as the ID of the information data IFD to the derived calculation value data CD, and outputs the calculation value data CD to the first RW control unit 75. The first derivation unit 76 derives the calculation value data CD each time new information data IFD is transmitted from the information acquisition apparatus 14.

The learning unit 77 receives the learning input data IDL, the quality data QD, and the machine learning model M from the first RW control unit 75. The learning unit 77 performs learning by inputting the learning input data IDL to the machine learning model M, and outputs a trained model TM.

The transmission control unit 78 receives the machine learning model M from the first RW control unit 75. The machine learning model M received by the transmission control unit 78 from the first RW control unit 75 is a trained model TM. The transmission control unit 78 performs a control for transmitting the trained model TM to the information processing apparatus 11.

Figure 13:
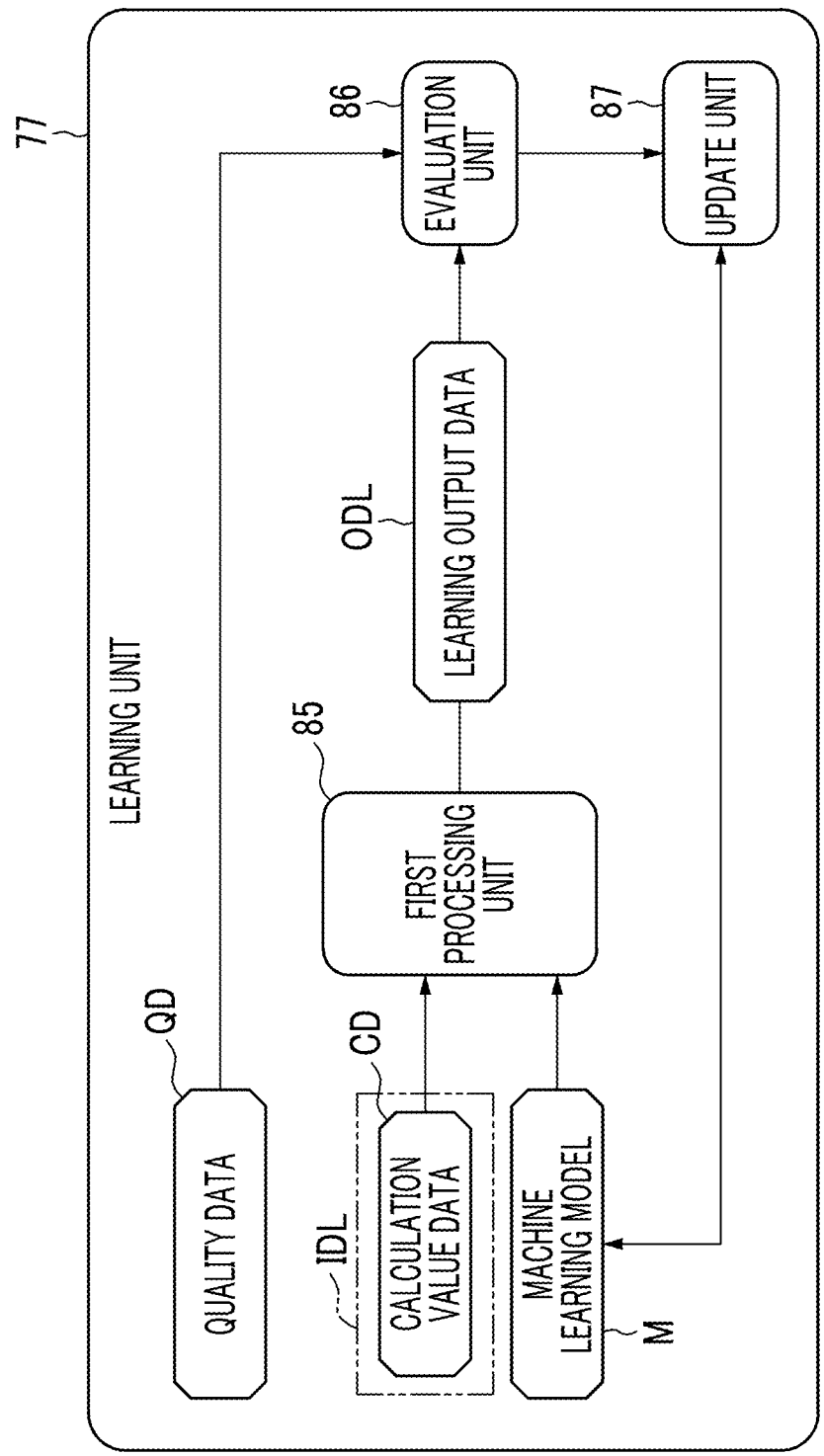
FIG. 13 is a diagram illustrating details of a learning unit.

As illustrated in FIG. 13, the learning unit 77 includes a first processing unit 85, an evaluation unit 86, and an update unit 87. The first processing unit 85 outputs learning output data ODL from the machine learning model M by inputting the learning input data IDL (calculation value data CD) to the machine learning model M. The learning output data ODL is, for example, a number-average molecular weight, similarly to the quality data QD. The first processing unit 85 outputs the learning output data ODL to the evaluation unit 86.

The evaluation unit 86 receives the learning output data ODL from the first processing unit 85. The evaluation unit 86 evaluates an accuracy of prediction of the machine learning model M by comparing the learning output data ODL and the quality data QD. The evaluation unit 86 outputs an evaluation result to the update unit 87.

The evaluation unit 86 evaluates an accuracy of prediction of the machine learning model M using, for example, a loss function. The loss function is a function that represents a degree of a difference between the learning output data ODL and the quality data QD. As a calculation value of the loss function is closer to 0, an accuracy of prediction of the machine learning model M is higher.

The update unit 87 updates the machine learning model M according to the evaluation result from the evaluation unit 86. For example, the update unit 87 changes various parameter values of the machine learning model M by a stochastic gradient descent method or the like using a learning coefficient. The learning coefficient indicates a change range in various parameter values of the machine learning model M. That is, as the learning coefficient has a relatively large value, the change range in various parameter values becomes wider, and thus, an update level of the machine learning model M becomes higher.

The inputting of the learning input data IDL to the machine learning model M and the outputting of the learning output data ODL to the evaluation unit 86 by the first processing unit 85, the evaluation of the accuracy of prediction by the evaluation unit 86, and the updating of the machine learning model M by the update unit 87 are repeated until the accuracy of prediction reaches a preset level. The machine learning model M of which the accuracy of prediction reaches a preset level is stored in the storage device 60A by the first RW control unit 75, as the trained model TM.

Figure 14:
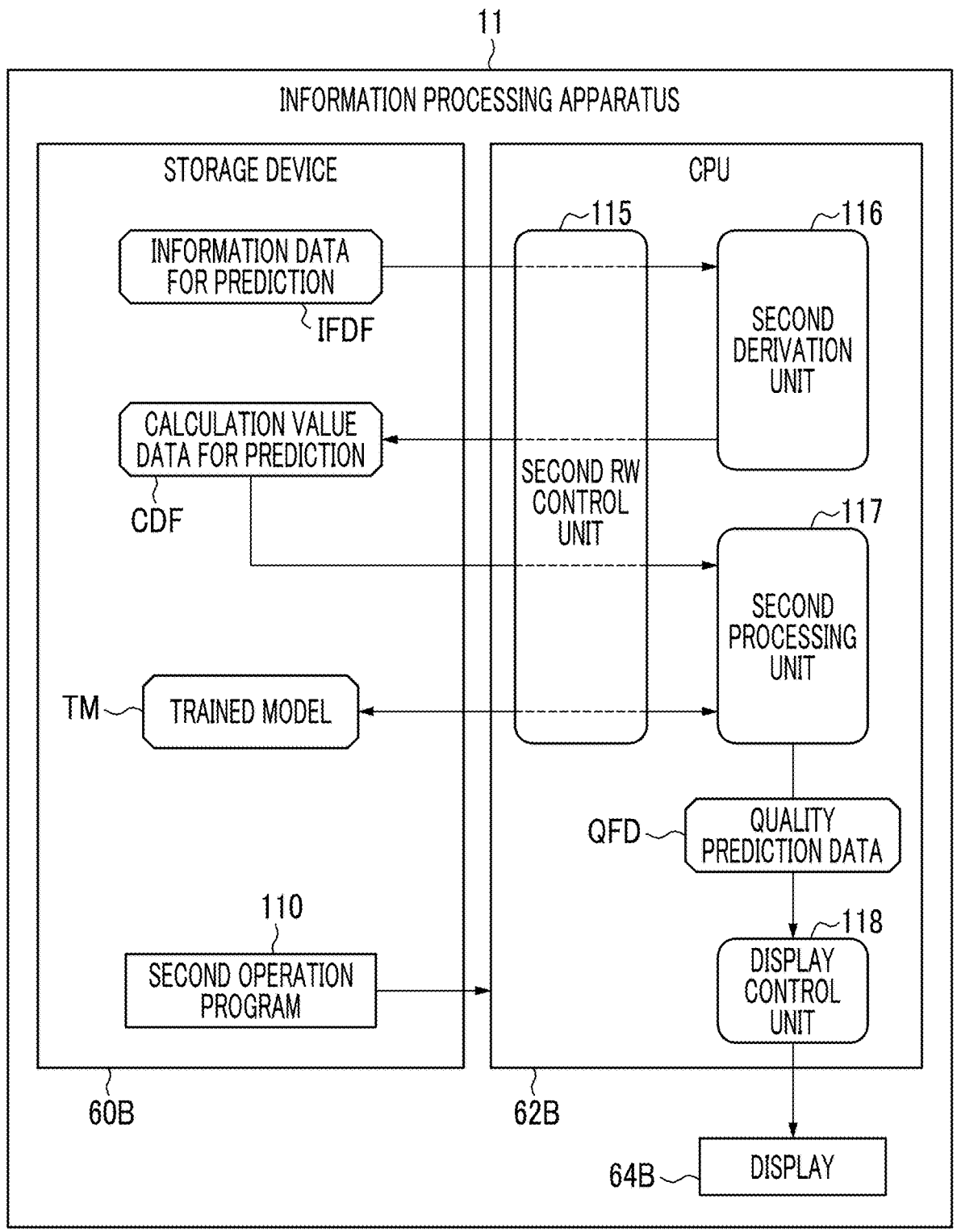
FIG. 14 is a block diagram illustrating a processing unit of a CPU of the information processing apparatus.

In FIG. 14, a second operation program 110 is stored in the storage device 60B of the information processing apparatus 11. The second operation program 110 is an application program for causing the computer to function as the information processing apparatus 11.

The storage device 60B also stores the trained model TM from the learning apparatus 10 and the information data for prediction IFDF from the information acquisition apparatus 14. Further, in the storage device 60B, the information data for prediction IFDF is information data of the product PR of which a quality is unknown and a quality is to be predicted by using the trained model TM.

Further, the storage device 60B also stores the calculation value data for prediction CDF derived from the information data for prediction IFDF.

In a case where the second operation program 110 is started, the CPU 62B of the computer including the information processing apparatus 11 functions as a second RW control unit 115, a second derivation unit 116, a second processing unit 117, and a display control unit 118 in cooperation with the memory 61 and the like.

Similar to the first RW control unit 75 of the learning apparatus 10, the second RW control unit 115 controls reading of various data stored in the storage device 60B and storing of various data in the storage device 60B. The second RW control unit 115 reads the information data for prediction IFDF from the storage device 60B (acquisition of information), and outputs the information data for prediction IFDF to the second derivation unit 116. Further, the second RW control unit 115 stores the calculation value data for prediction CDF from the second derivation unit 116 in the storage device 60B. In a case where the information data for prediction IFDF is a spectroscopic spectrum, the second derivation unit 116 may determine a wave number of a peak based on a quantum chemical calculation. At that time, a peak having a high contribution to the prediction accuracy may be extracted from a plurality of peaks by sparse modeling.

The second RW control unit 115 reads the trained model TM from the storage device 60B, and outputs the trained model TM to the second processing unit 117. The second RW control unit 115 acquires the trained model TM by reading the trained model TM from the storage device 60B.

The second RW control unit 115 reads the calculation value data for prediction CDF from the storage device 60B (acquisition of the calculation value), and outputs the read data to the second processing unit 117. The second RW control unit 115 acquires the calculation value data for prediction CDF by reading the calculation value data for prediction CDF from the storage device 60B.

The second derivation unit 116 receives the information data for prediction IFDF from the second RW control unit 115. The second derivation unit 116 derives the calculation value data for prediction CDF from the information data for prediction IFDF.

The second processing unit 117 receives the calculation value data for prediction CDF from the second RW control unit 115 and the trained model TM. The second processing unit 117 predicts a quality by inputting the calculation value data for prediction CDF to the trained model TM (prediction of the quality). The second processing unit 117 outputs quality prediction data QFD, which is a quality prediction result by the trained model TM, to the display control unit 118. The quality prediction data QFD is, for example, a number-average molecular weight, similarly to the quality data QD.

The display control unit 118 controls the display 64B to display the quality prediction data QFD and the like.

As described above, it is possible to predict a quality of a product obtained by a process including one or more pieces of processing.

Second Embodiment

In the second embodiment, a quality of a product is predicted by using processing condition data in addition to the calculation value data. Hereinafter, the second embodiment will be specifically described. On the other hand, except that the processing condition data, other parts are the same as those described in the first embodiment. Further, the flow processing apparatus, the information acquisition apparatus, and the quality evaluation apparatus in the second embodiment are the same as those in the first embodiment.

Figure 15:
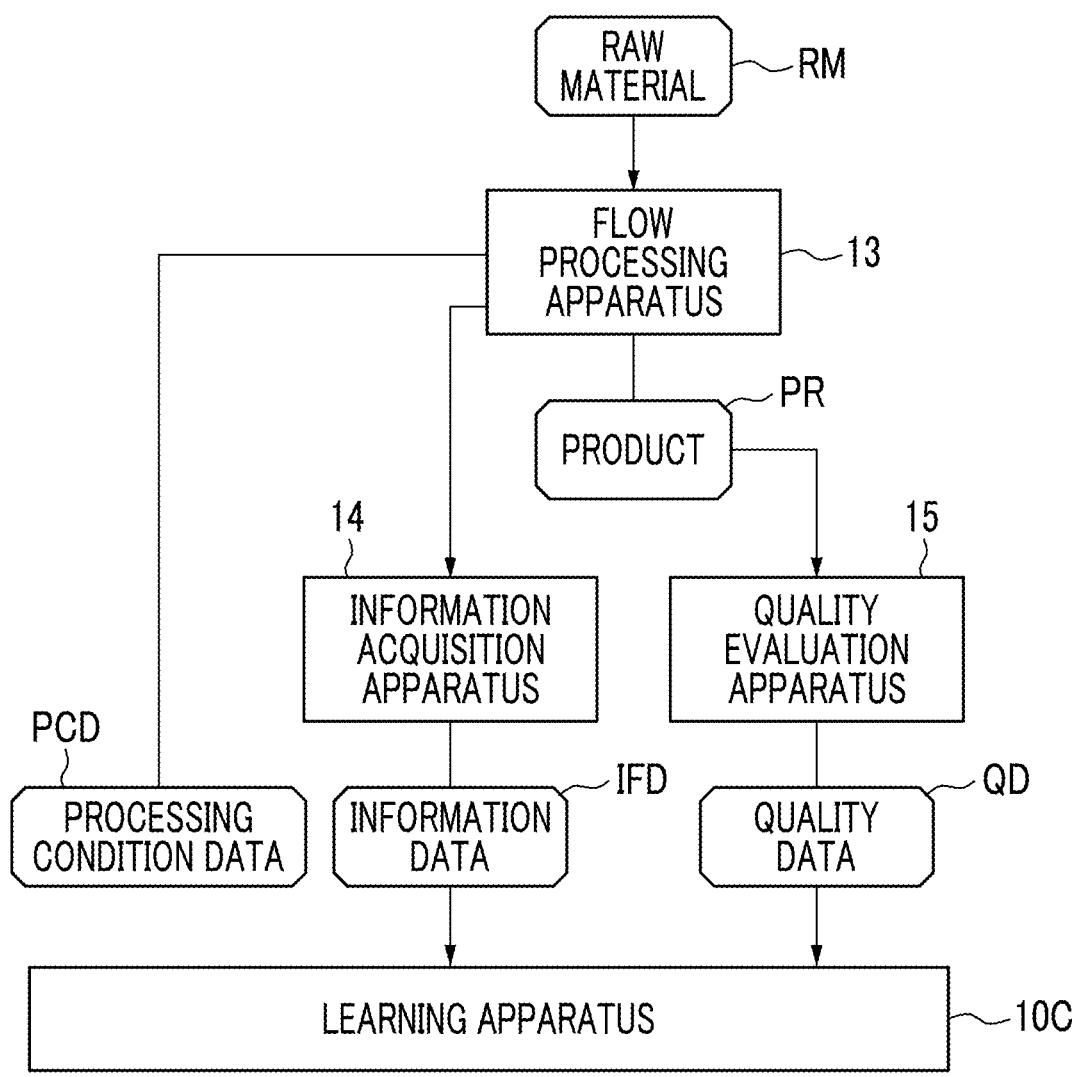
FIG. 15 is a diagram illustrating an outline of processing in the flow processing apparatus, the information acquisition apparatus, and the quality evaluation apparatus.

In FIG. 15, the flow processing apparatus 13 produces a product PR from a raw material RM according to processing condition data PCD by a process including the flow processing. In at least one piece of processing of the process, the information acquisition apparatus 14 acquires specific information at two points at which elapses of processing times between before the processing and after the processing are different from each other, and outputs acquired information data IFD. The quality evaluation apparatus 15 evaluates the quality of the product PR and outputs the quality data QD which is the evaluation result. The processing condition data PCD from the flow processing apparatus 13, the information data IFD from the information acquisition apparatus 14, and the quality data QD from the quality evaluation apparatus 15 are respectively transmitted to the learning apparatus 10C.

Figure 16:
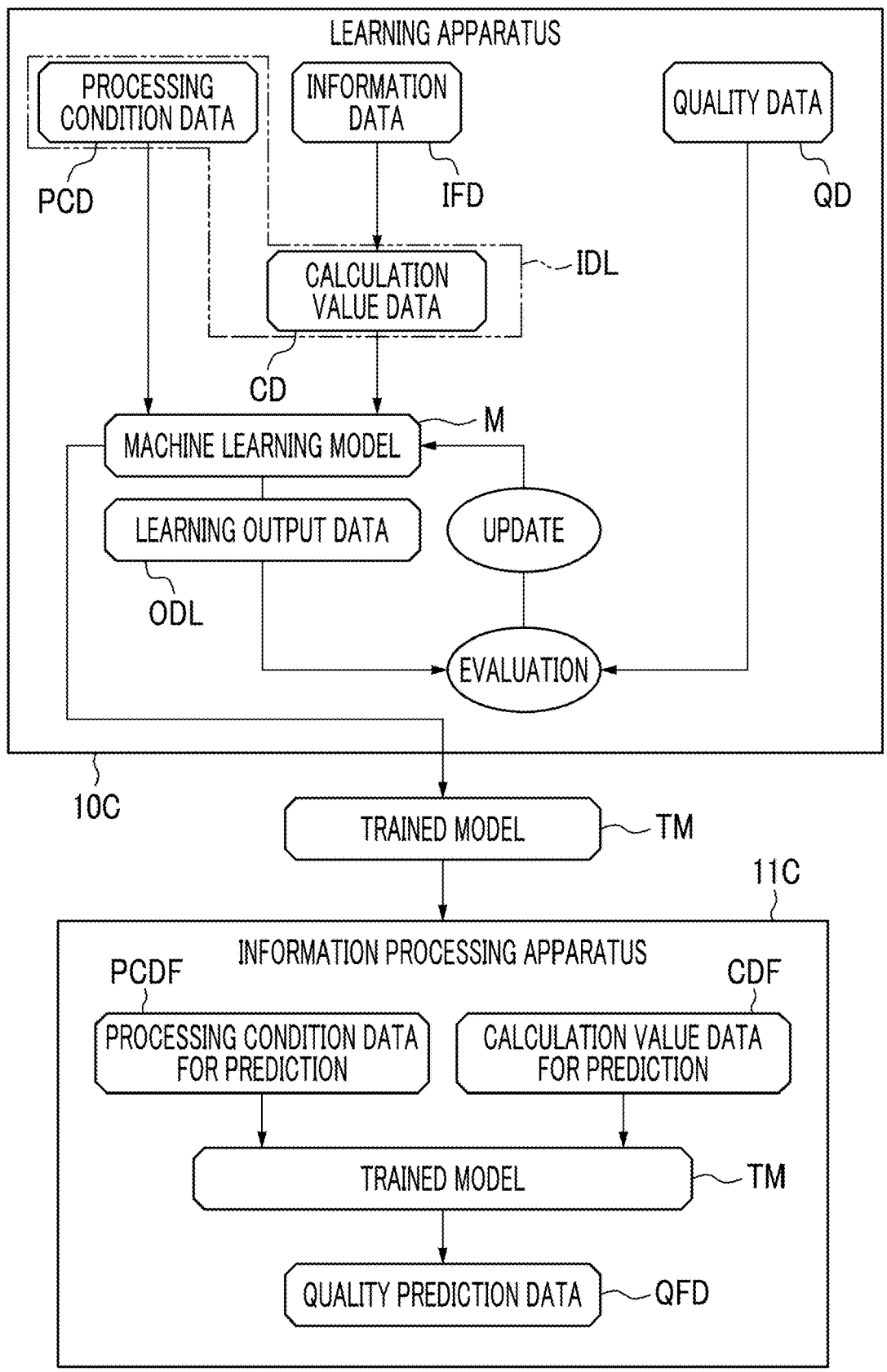
FIG. 16 is a diagram illustrating an outline of processing in the information processing apparatus and the learning apparatus.
Figure 17:
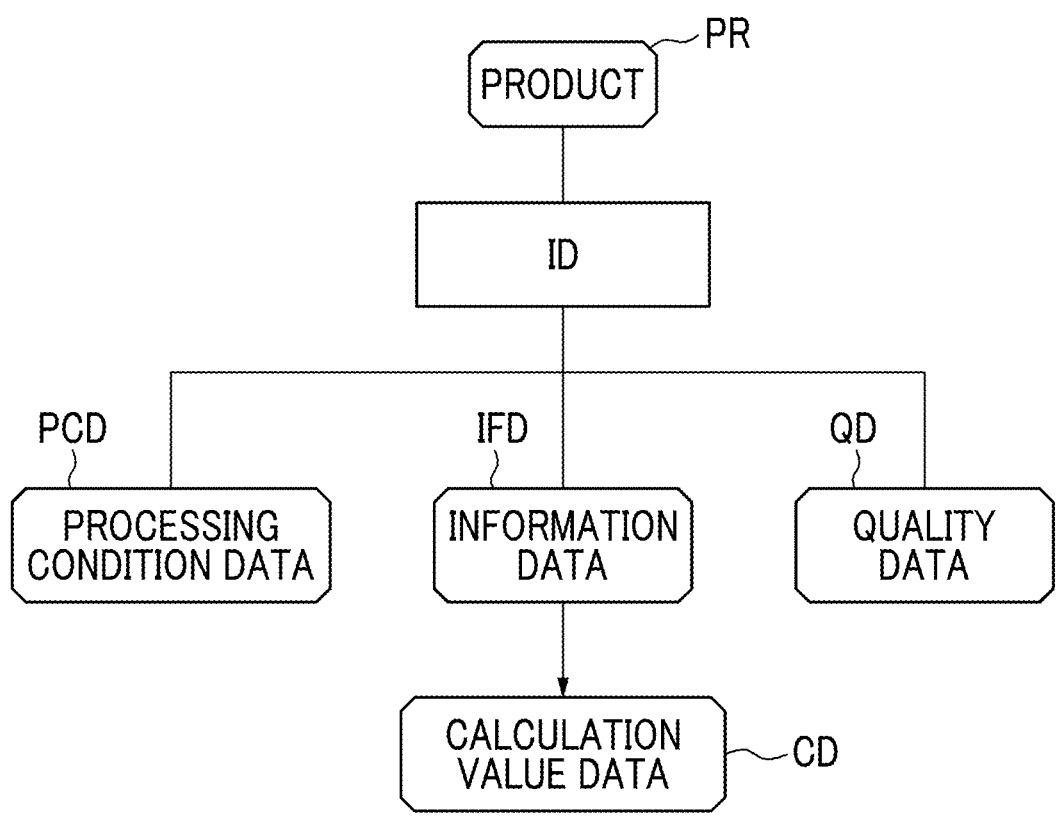
FIG. 17 is a diagram illustrating that information data, calculation value data, processing condition data, and quality data are associated with a common ID.

In FIG. 16, the learning apparatus 10C acquires the processing condition data PCD from the flow processing apparatus 13, the information data IFD from the information acquisition apparatus 14, and the quality data QD from the quality evaluation apparatus 15. The learning apparatus 10C derives the calculation value data CD of the difference from the information data IFD. It is assumed that the processing condition data PCD and the calculation value data CD correspond to the learning input data IDL. As illustrated in FIG. 17, the processing condition data PCD, the information data IFD, the calculation value data CD derived from the information data IFD, and the quality data QD are associated with common ID which is assigned to one product PR. The processing condition data PCD, the calculation value data CD, and the quality data QD are included in a known data set.

The information processing apparatus 11C receives the trained model TM from the learning apparatus 10C. The information processing apparatus 11C inputs, to the trained model TM, the processing condition data for prediction PCDF, which is processing condition data of a product PR of which a quality is unknown, and the calculation value data for prediction CDF, which is calculation value data of the product PR of which a quality is unknown. The calculation value data for prediction CDF is data derived from the information data for prediction IFDF, which is information data IFD of the product PR of which a quality is unknown, similar to the calculation value data CD. The trained model TM outputs quality prediction data QFD according to the processing condition data for prediction PCDF and the calculation value data for prediction CDF.

Figure 18:
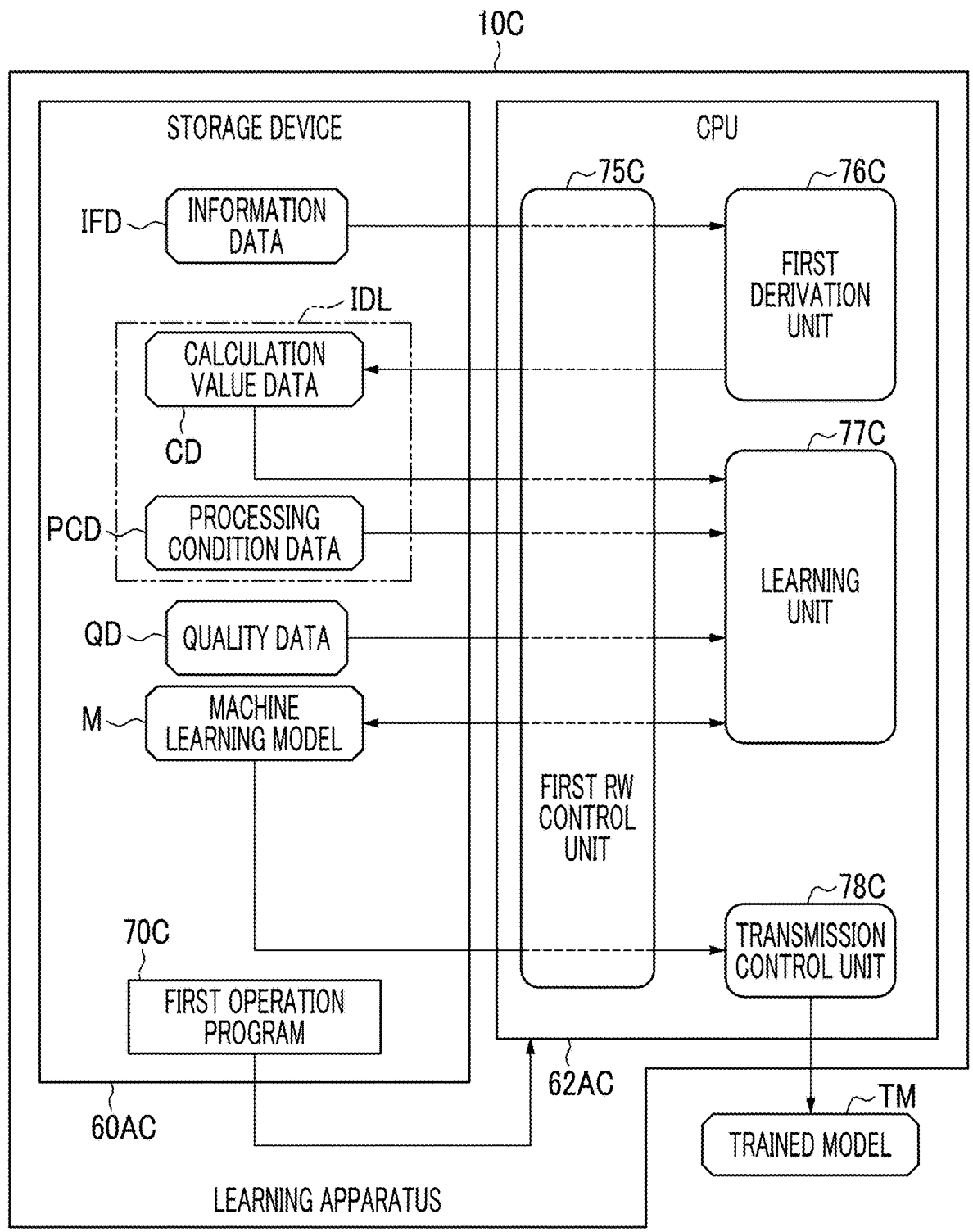
FIG. 18 is a block diagram illustrating the processing unit of the CPU of the learning apparatus.

In FIG. 18, the storage device 60AC of the learning apparatus 10C stores the processing condition data PCD from the flow processing apparatus 13, the information data IFD from the information acquisition apparatus 14, and the quality data QD from the quality evaluation apparatus 15. The calculation value data CD derived from the information data IFD and the machine learning model M are also stored. A plurality of sets of the processing condition data PCD, the information data IFD, the calculation value data CD, and the quality data QD are stored in the storage device 60AC.

The first RW control unit 75C reads the calculation value data CD, the processing condition data PCD, and the quality data QD from the storage device 60AC, and outputs the read data to the learning unit 77C. In addition, the first RW control unit 75C reads the machine learning model M from the storage device 60AC, and outputs the machine learning model M to any of the learning unit 77C and the transmission control unit 78C. Further, the first RW control unit 75C stores the machine learning model M from the learning unit 77C in the storage device 60AC.

Figure 19:
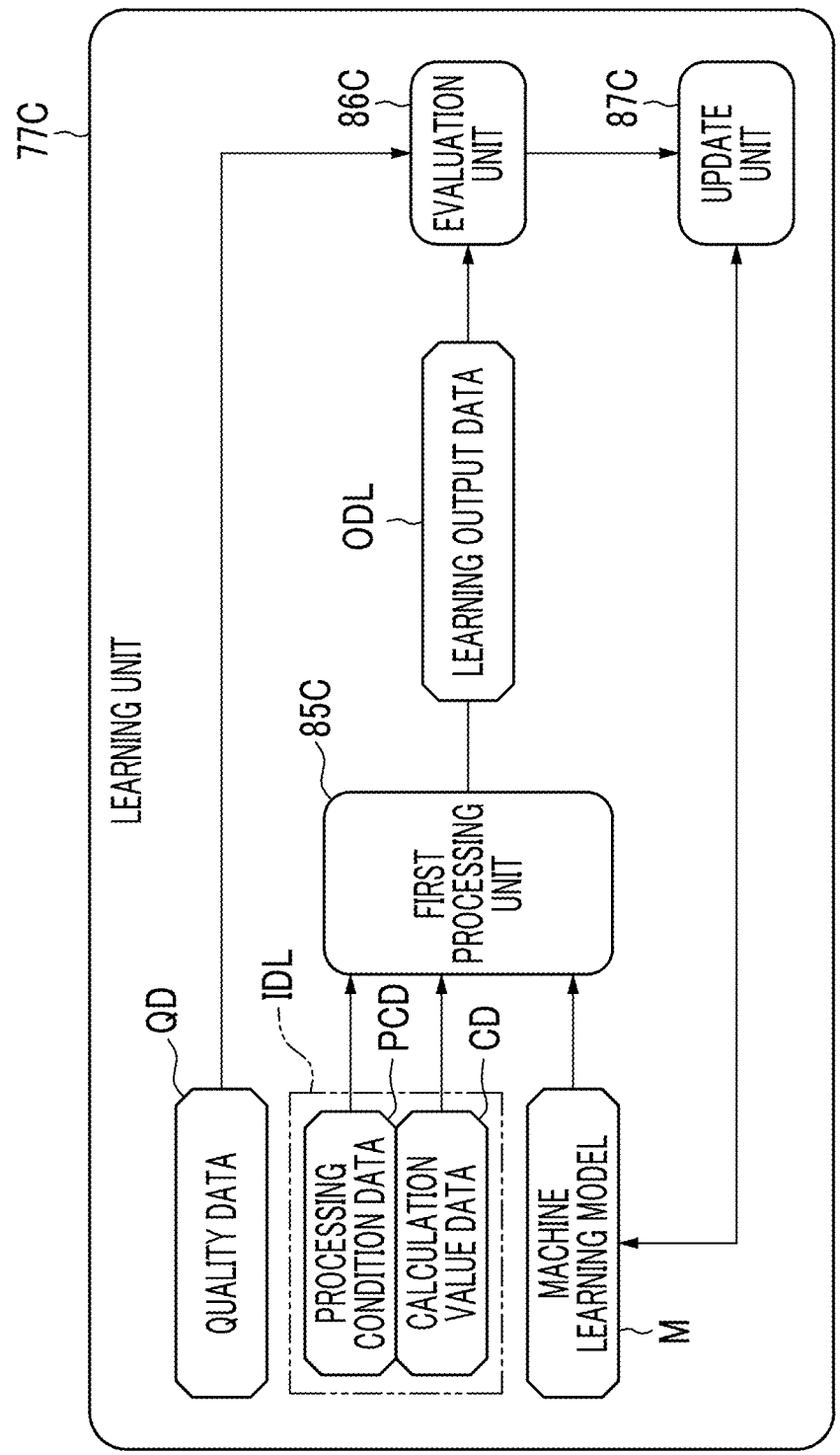
FIG. 19 is a diagram illustrating details of the learning unit.

As illustrated in FIG. 19, the learning unit 77C includes a first processing unit 85C, an evaluation unit 86C, and an update unit 87C. The first processing unit 85C outputs learning output data ODL from the machine learning model M by inputting the learning input data IDL (the processing condition data PCD and the calculation value data CD) to the machine learning model M. The learning output data ODL is, for example, a number-average molecular weight, similarly to the quality data QD. The first processing unit 85C outputs the learning output data ODL to the evaluation unit 86C. The machine learning model M of which the accuracy of prediction reaches a preset level is stored in the storage device 60AC by the first RW control unit 75C, as the trained model TM.

Figure 20:
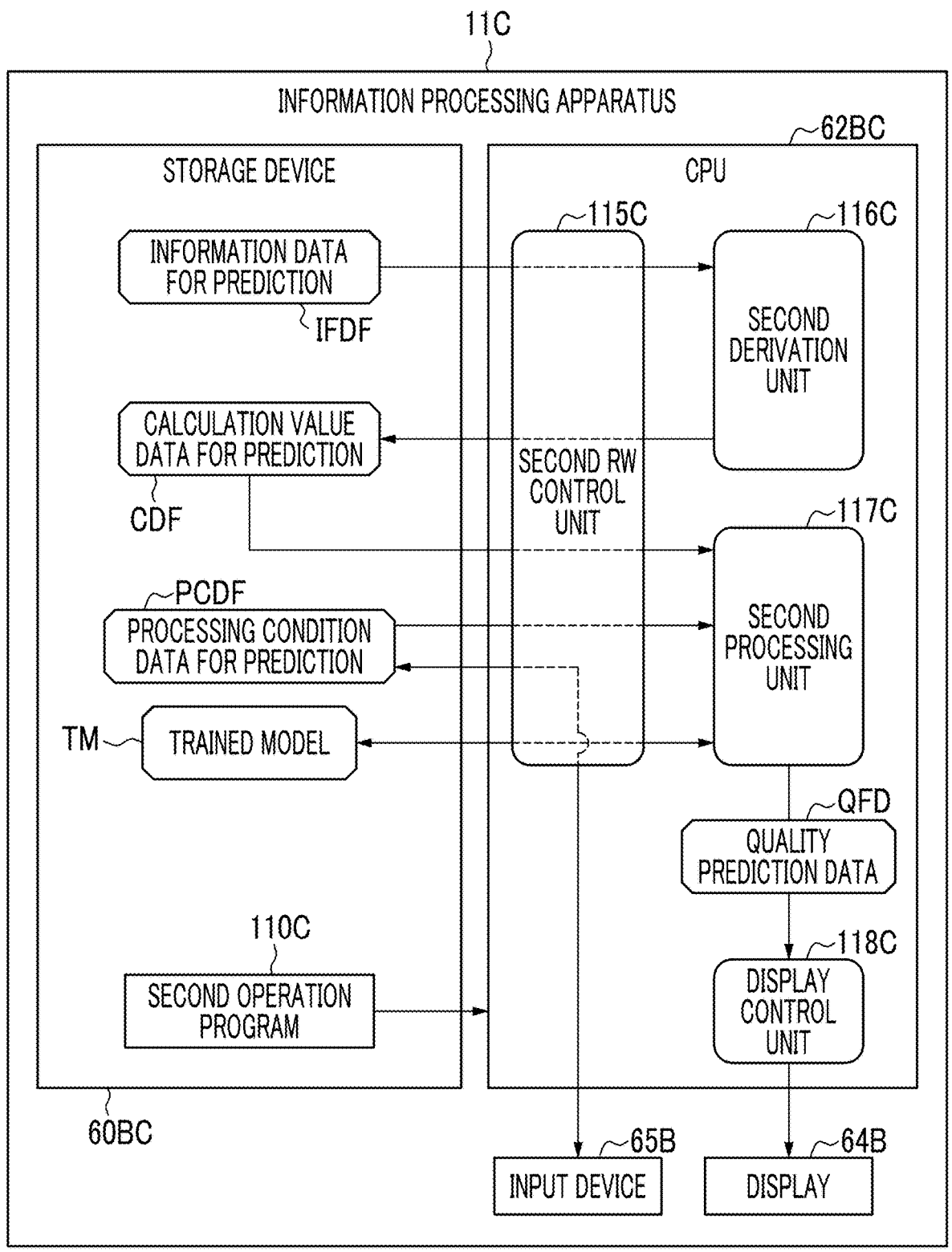
FIG. 20 is a block diagram illustrating the processing unit of the CPU of the information processing apparatus.

In FIG. 20, the storage device 60BC of the information processing apparatus 11C also stores the trained model TM from the learning apparatus 10C and the information data for prediction IFDF from the information acquisition apparatus 14. In addition, the storage device 60BC also stores the processing condition data for prediction PCDF. The processing condition data for prediction PCDF may be input via the input device 65B by the operator. More specifically, an input screen including input boxes for each item of the processing condition data for prediction PCDF may be displayed on the display 64B, and the processing condition data for prediction PCDF may be input via the input screen. The processing condition data for prediction PCDF and the information data for prediction IFDF are the processing condition data and the information data of the product PR of which a quality is unknown and a quality is to be predicted by using the trained model TM.

Further, the storage device 60BC also stores the calculation value data for prediction CDF derived from the information data for prediction IFDF.

In a case where the second operation program 110C is started, the CPU 62BC of the computer including the information processing apparatus 11C functions as a second RW control unit 115C, a second derivation unit 116C, a second processing unit 117C, and a display control unit 118C in cooperation with the memory 61 and the like.

Similar to the first RW control unit 75C of the learning apparatus 10C, the second RW control unit 115C controls reading of various data stored in the storage device 60BC and storing of various data in the storage device 60BC. The second RW control unit 115C reads the information data for prediction IFDF from the storage device 60BC (acquisition of information), and outputs the information data for prediction IFDF to the second derivation unit 116C. Further, the second RW control unit 115C stores the calculation value data for prediction CDF from the second derivation unit 116C in the storage device 60BC. The storage device 60BC may store an autoencoder, and the calculation value data may be derived from information data such as an image by using the autoencoder.

The second RW control unit 115C reads the trained model TM from the storage device 60BC, and outputs the trained model TM to the second processing unit 117C. The second RW control unit 115C acquires the trained model TM by reading the trained model TM from the storage device 60BC.

The second RW control unit 115C reads the calculation value data for prediction CDF and the processing condition data for prediction PCDF from the storage device 60BC (acquisition of the calculation value, acquisition of the condition value), and outputs the read data to the second processing unit 117C. The second RW control unit 115C acquires the calculation value data for prediction CDF and the processing condition data for prediction PCDF by reading the calculation value data for prediction CDF and the processing condition data for prediction PCDF from the storage device 60BC.

The second derivation unit 116C receives the information data for prediction IFDF from the second RW control unit 115C. The second derivation unit 116C derives the calculation value data for prediction CDF from the information data for prediction IFDF.

The second processing unit 117C receives the processing condition data for prediction PCDF, the calculation value data for prediction CDF, and the trained model TM from the second RW control unit 115C. The second processing unit 117C predicts a quality by inputting the processing condition data for prediction PCDF and the calculation value data for prediction CDF to the trained model TM (prediction of the quality). The second processing unit 117C outputs quality prediction data QFD, which is a quality prediction result by the trained model TM, to the display control unit 118C. The quality prediction data QFD is, for example, a number-average molecular weight, similarly to the quality data QD.

As described above, it is possible to predict a quality of a product obtained by a process including one or more pieces of processing. Further, in the second embodiment, a quality of a product is predicted by using the processing condition data in addition to the calculation value data. Therefore, it is possible to predict the quality with higher accuracy than in the first embodiment.

In each of the embodiments, the processing condition which is received by the setting unit 25 of the flow processing apparatus 13 is used as the processing condition data PCD. On the other hand, the present disclosure is not limited thereto. As the processing condition data PCD, actual measurement values that are measured by the first flow velocity sensor 35, the second flow velocity sensor 36, the third flow velocity sensor 37, and the temperature sensor 38 may be used.

In each of the embodiments, the quality prediction display screen 120 is exemplified as an output form of the quality prediction data QFD. On the other hand, the present disclosure is not limited thereto. Instead of or in addition to the quality prediction display screen 120, a form in which the quality prediction data QFD is printed and output on a paper medium and a form in which the quality prediction data QFD is output as a data file may be adopted.

The hardware configuration of each of the computers including the learning apparatuses 10 and 10C and the information processing apparatuses 11 and 11C may be modified in various ways.

For example, the learning apparatus 10 and the information processing apparatus 11 may be integrated and configured by one computer. Further, at least one of the learning apparatus 10 or the information processing apparatus 11 may be configured by a plurality of computers which are separated as hardware for the purpose of improving processing capability and reliability. For example, in the learning apparatus 10, the function of the first derivation unit 76 and the function of the learning unit 77 are distributed to two computers. In this case, the learning apparatus 10 is configured by two computers. The configuration is the same for the learning apparatus 10C and the information processing apparatus 11C.

In this way, the hardware configuration of the computer of each of the learning apparatuses 10 and 10C and the information processing apparatuses 11 and 11C may be appropriately changed according to the required performance such as processing capability, safety, and reliability. Further, not only hardware but also the application program such as the first operation programs 70 and 70C and the second operation programs 110 and 110C, may be duplicated or distributed and stored in a plurality of storage devices for the purpose of ensuring safety and reliability.

In each of the embodiments, for example, as a hardware structure of the processing unit that executes various processing, such as the first RW control units 75 and 75C, the first derivation units 76 and 76C, the learning units 77 and 77C, the transmission control units 78 and 78C, the second RW control units 115 and 115C, the second derivation units 116 and 116C, the second processing units 117 and 117C, and the display control unit 118, the following various processors may be used. The various processors include, as described above, the CPU 62A, 62AC, 62B, or 62BC which is a general-purpose processor that functions as various processing units by executing software (the first operation programs 70 and 70C, and the second operation programs 110 and 110C), a programmable logic device (PLD) such as a field programmable gate array (FPGA) which is a processor capable of changing a circuit configuration after manufacture, a dedicated electric circuit such as an application specific integrated circuit (ASIC) which is a processor having a circuit configuration specifically designed to execute specific processing, and the like.

One processing unit may be configured by one of these various processors, or may be configured by a combination of two or more processors having the same type or different types (for example, a combination of a plurality of FPGAs and/or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as typified by system on chip (System On Chip: SoC), there is a form in which a processor that realizes the functions of the entire system including a plurality of processing units with one IC (Integrated Circuit) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

Further, the quality prediction by the information processing apparatus can also be suitably used for a search apparatus configured to search for the processing condition such that a desired quality can be obtained based on the prediction result.

Modification Example

Figure 21:
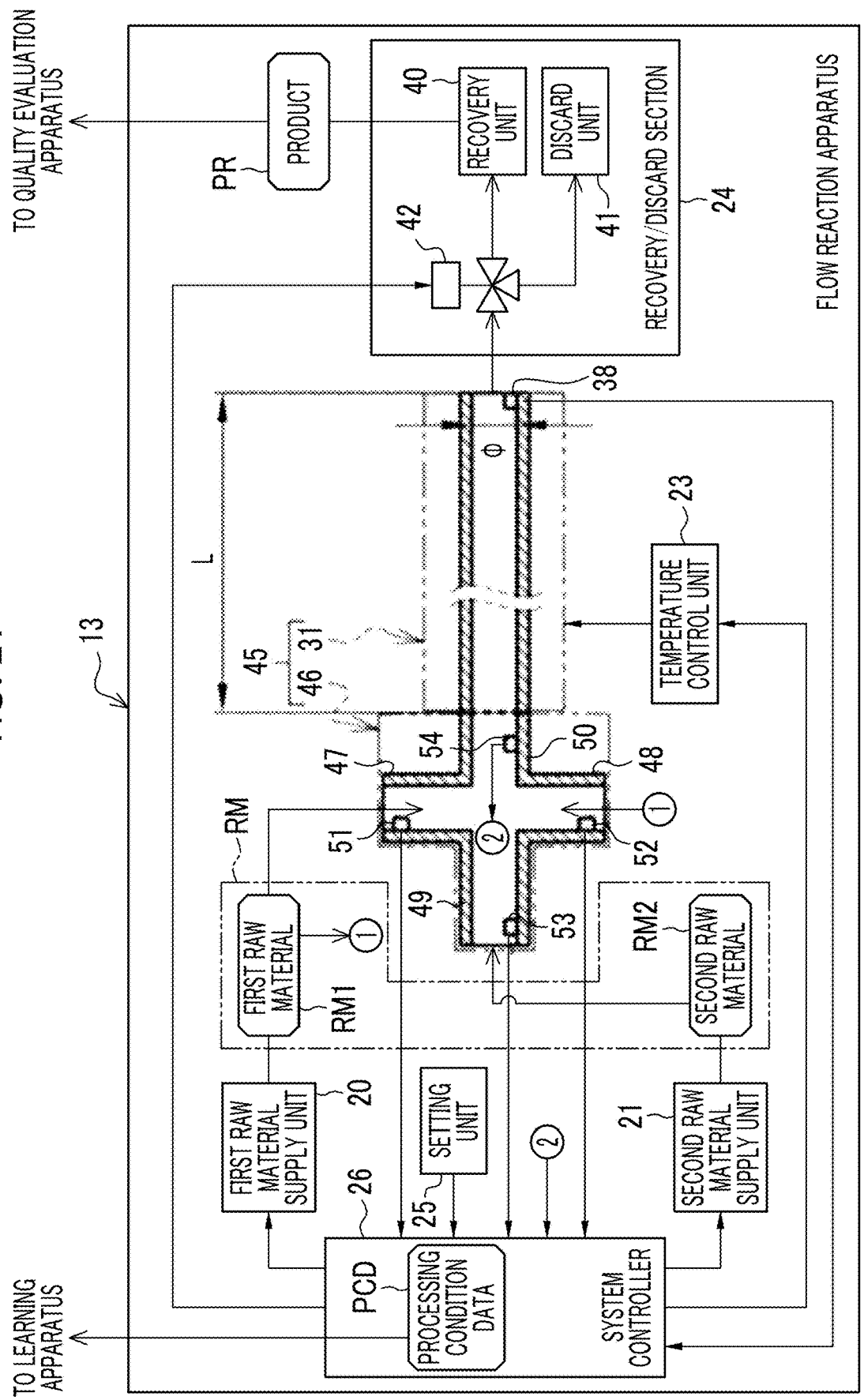
FIG. 21 is a diagram illustrating the flow processing apparatus with a processing section including a cross-shaped junction portion.

Instead of the processing section 22, a processing section 45 illustrated in FIG. 21 may be used. In FIG. 21, the same components as those in FIG. 10 are denoted by the same reference numerals, and a description thereof will be omitted.

The junction portion 46 of the processing section 45 illustrated in FIG. 21 includes a first pipe portion 47, a second pipe portion 48, a third pipe portion 49, and a fourth pipe portion 50. The first pipe portion 47 and the second pipe portion 48 are connected in a straight line. Similarly, the third pipe portion 49 and the fourth pipe portion 50 are connected in a straight line. The first pipe portion 47 intersects with the third pipe portion 49 at a right angle, and the second pipe portion 48 intersects with the fourth pipe portion 50 at a right angle. That is, the junction portion 46 has a cross shape.

The first pipe portion 47 and the second pipe portion 48 are connected to the first raw material supply unit 20, and the third pipe portion 49 is connected to the second raw material supply unit 21. Further, the fourth pipe portion 50 is connected to the reaction portion 31. The first raw material RM1 is supplied from the first raw material supply unit 20 to the first pipe portion 47 and the second pipe portion 48, and the second raw material RM2 is supplied from the second raw material supply unit 21 to the third pipe portion 49. The first raw material RM1 and the second raw material RM2 are mixed in the fourth pipe portion 50, and are transported to the reaction portion 31 in a mixed state.

A first flow velocity sensor 51 and a second flow velocity sensor 52 that detect the flow velocity of the first raw material RM1 passing through the first pipe portion 47 and the second pipe portion 48 are provided in the first pipe portion 47 and the second pipe portion 48. In addition, a third flow velocity sensor 53 that detects the flow velocity of the second raw material RM2 passing through the third pipe portion 49 is provided in the third pipe portion 49. In addition, a fourth flow velocity sensor 54 that detects a flow velocity of a raw material mixture passing through the fourth pipe portion 50 is provided in the fourth pipe portion 50.

In this case, the system controller 26 adjusts the flow rate of the first raw material RM1 by controlling the rotation speed of the pump of the first raw material supply unit 20 according to an average value of the flow velocity of the first raw material RM1 that is detected by the first flow velocity sensor 51 and the flow velocity of the first raw material RM1 that is detected by the second flow velocity sensor 52. Further, the system controller 26 adjusts the flow rate of the second raw material RM2 by controlling the rotation speed of the pump of the second raw material supply unit 21 according to the flow velocity of the second raw material RM2 that is detected by the third flow velocity sensor 53.

In a case where the processing section 45 is used, the system controller 26 adjusts the flow rate of the first raw material RM1 by controlling the rotation speed of the pump of the first raw material supply unit 20 such that an average value of the flow velocity of the first raw material RM1 detected by the first flow velocity sensor 51 and the flow velocity of the first raw material RM1 detected by the second flow velocity sensor 52 matches with the flow velocity of the first raw material RM1 registered in the processing condition data PCD. Similarly, the system controller 26 adjusts the flow rate of the second raw material RM2 by controlling the rotation speed of the pump of the second raw material supply unit 21 such that the flow velocity of the second raw material RM2 detected by the third flow velocity sensor 53 matches with the flow velocity of the second raw material RM2 registered in the processing condition data PCD.

Information Processing Method

According to the present disclosure, there is provided an information processing method that predicts a quality of a product obtained by a process including one or more pieces of processing, the method including: acquiring, in at least one piece of processing of the process, at least one piece of information of chemical information or physical information of an object to be processed and a processed object at two points at which elapses of processing times between before the processing and after the processing are different from each other; acquiring a calculation value of a difference between numerical values at the two points that are obtained from the information; and setting the difference as an explanatory variable, setting the quality of the product as an objective variable, and predicting the quality of the product based on the calculation value by using a trained model obtained by performing machine learning based on a known data set of the explanatory variable and the objective variable.

Each configuration of the information processing method is derived from the configuration described above in the information processing apparatus.

Program

According to the present disclosure, there is provided a program causing a computer to execute information processing of predicting a quality of a product obtained by a process including one or more pieces of processing, the information processing including: acquiring, in at least one piece of processing of the process, at least one piece of information of chemical information or physical information of an object to be processed and a processed object at two points at which elapses of processing times between before the processing and after the processing are different from each other; acquiring a calculation value of a difference between numerical values at the two points that are obtained from the information; and setting the difference as an explanatory variable, setting the quality of the product as an objective variable, and predicting the quality of the product based on the calculation value by using a trained model obtained by performing machine learning based on a known data set of the explanatory variable and the objective variable.

Each configuration of the information processing method is derived from the configuration described above in the information processing apparatus.

EXAMPLES

Hereinafter, the present disclosure will be described in more detail with reference to examples. Here, the present disclosure is not limited to these examples.

In order to demonstrate high accuracy of the quality prediction by the information processing according to the present disclosure, on the assumption of a polymer synthesis process using the flow processing apparatus 13 illustrated in FIG. 10, prediction of a number-average molecular weight (quality) of polystyrene (product) is performed with comparative examples. The data used for the quality prediction will be described in (1) to (3) below.

(1) Infrared Spectroscopic Spectrum

At the $a_2$ point before the second flow processing and the $d_2$ point after the second flow processing, as the chemical information, an infrared spectroscopic spectrum as illustrated in FIG. 3 is acquired. The acquisition of the infrared spectroscopic spectrum is performed at points described in level number 1 to level number 10 as illustrated in FIG. 22, and the processing conditions are different from each other in each level as illustrated in FIG. 25. The difference in the integrated intensity of the peaks (hereinafter, may be simply referred to as "integrated intensity"), which is a numerical value obtained from the infrared spectroscopic spectrum, is set as an explanatory variable, and as illustrated in FIG. 23, the calculation value data of the difference is acquired. At that time, characteristic wave numbers in the reaction are determined by a quantum chemical calculation, and peaks form a peak A to a peak N in the infrared spectroscopic spectrum corresponding to the determined wave numbers are specified. Further, these wave numbers include wave numbers derived from by-products, that is, these peaks include peaks derived from by-products. A peak A to a peak C are derived from a C—H expansion and contraction of an aromatic ring, and a peak D and a peak E are derived from a C—H expansion and contraction of an aliphatic. A peak F to a peak I are derived from a mono-substituted product of an aromatic ring, and a peak J and a peak K are derived from a C=C expansion and contraction of an aromatic ring. A peak L is derived from a C—H variation angle, a peak M is derived from C—H out-of-plane variation angle, and a peak N is derived from a variation angle of an aromatic ring. In FIG. 22 and FIG. 23, data related to peaks of a peak D to a peak M is omitted.

(2) Mixing Ratio (State Quantity of Flow Field)

At a $b_1$ point during the first flow processing and a $d_1$ point after the first flow processing, a mixing ratio (a state quantity of a flow field) is acquired as physical information. The numerical value obtained from the mixing ratio, here, the difference of the mixing ratio itself is set as an explanatory variable, and as illustrated in FIG. 24, the calculation value data of the difference is acquired. The level numbers illustrated in FIG. 24 correspond to the level numbers illustrated in FIG. 22 and FIG. 23.

The mixing ratio is obtained by simulating a mixed state of the first raw material RM1 (solution obtained by dissolving polystyryl lithium in a solvent) and the second raw material RM2 (methanol) by a computational fluid dynamics analysis. Specifically, a region in which the two raw materials (the first raw material RM1 and the second raw material RM2) exist without being mixed and a region in which the two raw materials are mixed (mixed region) are imaged. The mixed state is imaged by displaying the first raw material RM1 in white, displaying the second raw material RM2 in black, and further displaying the mixed region in gray. The mixing ratio is obtained from an area of the mixed region with respect to an area of the entire region.

(3) Processing Condition

As illustrated in FIG. 25, processing conditions corresponding to the level number 1 to the level number 10 illustrated in FIG. 22 and FIG. 23 are prepared.

Example 1

By using the information processing apparatus 11 described in the first embodiment, a number-average molecular weight (a quality) of polystyrene (a product) obtained by the polymer synthesis process is predicted. The learning apparatus 10, the flow processing apparatus 13, and other configurations are also as described in the first embodiment. As a machine learning algorithm, a gradient boosting regressor using a scikit-learn library of python is used.

By setting the differences in the level number 2 to the level number 10 illustrated in FIG. 23 as the explanatory variable, setting the number-average molecular weight as the objective variable, and using the trained model TM obtained by performing machine learning based on known data sets of the explanatory variable and the objective variable, based on the calculation value described in the level number 1, the number-average molecular weight of polystyrene of the level number 1 is predicted.

For the level number 2, based on known data sets obtained from levels other than the level number 2, the number-average molecular weight of polystyrene is predicted in the same manner as above. The same operation is repeated, and thus the number-average molecular weights of polystyrenes corresponding to the level number 3 to the level number 10 is predicted.

A determination coefficient is obtained from the predicted values of the number-average molecular weights corresponding to the level number 1 to the level number 10 and the number-average molecular weights illustrated in FIG. 23. The results are illustrated in FIG. 26.

Comparative Example 1

Except that the integrated intensity at the $d_2$ point illustrated in FIG. 22 is used as the explanatory variable instead of the difference, in the same manner as in Example 1, the number-average molecular weights corresponding to the level number 1 to the level number 10 are predicted, and the determination coefficient is obtained. The results are illustrated in FIG. 26.

Example 2

By using the information processing apparatus 11C described in the second embodiment, a number-average molecular weight (a quality) of polystyrene (a product) obtained by the polymer synthesis process is predicted. The learning apparatus 10C, the flow processing apparatus 13, and other configurations are also as described in the second embodiment. The machine learning algorithm is the same as in the Example 1.

By setting the differences in the level number 2 to the level number 10 illustrated in FIG. 23 and the processing conditions in the level number 2 to the level number 10 illustrated in FIG. 25 as the explanatory variable, setting the number-average molecular weight as the objective variable, and using the trained model TM obtained by performing machine learning based on known data sets of the explanatory variable and the objective variable, based on the calculation value described in the level number 1 and the condition value, the number-average molecular weight of polystyrene of the level number 1 is predicted.

For the level number 2, based on known data sets obtained from levels other than the level number 2, the number-average molecular weight of polystyrene is predicted in the same manner as above. The same operation is repeated, and thus the number-average molecular weight of polystyrene corresponding to each of the level number 3 to the level number 10 is predicted.

A determination coefficient is obtained from the predicted values of the number-average molecular weights corresponding to the level number 1 to the level number 10 and the number-average molecular weights illustrated in FIG. 23. The results are illustrated in FIG. 26.

Comparative Example 2

Except that the integrated intensity at the $d_2$ point illustrated in FIG. 22 is used as the explanatory variable instead of the difference, in the same manner as in Example 2, the number-average molecular weights corresponding to the level number 1 to the level number 10 are predicted, and the determination coefficient is obtained. The results are illustrated in FIG. 26.

Example 3

By using the information processing apparatus 11C described in the second embodiment, a number-average molecular weight (a quality) of polystyrene (a product) obtained by the polymer synthesis process is predicted. The learning apparatus 10C, the flow processing apparatus 13, and other configurations are also as described in the second embodiment. The machine learning algorithm is the same as in the Example 1.

By setting the differences in the level number 2 to the level number 10 illustrated in FIG. 24 and the processing conditions in the level number 2 to the level number 10 illustrated in FIG. 25 as the explanatory variable, setting the number-average molecular weight as the objective variable, and using the trained model TM obtained by performing machine learning based on known data sets of the explanatory variable and the objective variable, based on the calculation value described in the level number 1 and the condition value, the number-average molecular weight of polystyrene of the level number 1 is predicted.

For the level number 2, based on known data sets obtained from levels other than the level number 2, the number-average molecular weight of polystyrene is predicted in the same manner as above. The same operation is repeated, and thus the number-average molecular weight of polystyrene corresponding to each of the level number 3 to the level number 10 is predicted.

A determination coefficient is obtained from the predicted values of the number-average molecular weights corresponding to the level number 1 to the level number 10 and the number-average molecular weights illustrated in FIG. 24. The results are illustrated in FIG. 26.

Comparative Example 3

Except that the mixing ratio at the $b_1$ point illustrated in FIG. 24 is used as the explanatory variable instead of the difference, in the same manner as in Example 3, the number-average molecular weights corresponding to the level number 1 to the level number 10 are predicted, and the determination coefficient is obtained. The results are illustrated in FIG. 26.

As can be seen from Example 1 and Comparative Example 1, Example 1 in which the calculation value of the difference in the integrated intensity is set as an explanatory variable has a higher determination coefficient than in Comparative Example 1 in which the integrated intensity itself is set as an explanatory variable. Therefore, Example 1 has higher quality prediction accuracy. The same applies to a comparison between Example 2 and Comparative Example 2 and a comparison between Example 3 and Comparative Example 3. Therefore, Example 2 and Example 3 have higher prediction accuracy.

Further, as can be seen from Example 1 and Example 2, in Example 2 in which the processing condition is set as the explanatory variable in addition to the calculation value of the difference in the integrated intensity, the determination coefficient is higher than that in Example 1. Therefore, Example 2 is superior in quality prediction accuracy.

The technique of the present disclosure can also appropriately combine the various embodiments and the various modification examples. In addition, the technique of the present disclosure is not limited to each embodiment, and various configurations may be adopted without departing from the scope of the present disclosure. Further, the technique of the present disclosure extends to a program and a storage medium for non-temporarily storing the program.

The described contents and the illustrated contents are detailed explanations of a part according to the technique of the present disclosure, and are merely examples of the technique of the present disclosure. For example, the descriptions related to the configuration, the function, the operation, and the effect are descriptions related to examples of a configuration, a function, an operation, and an effect of a part according to the technique of the present disclosure. Therefore, it goes without saying that, in the described contents and illustrated contents, unnecessary parts may be deleted, new components may be added, or replacements may be made without departing from the spirit of the technique of the present disclosure. Further, in order to avoid complications and facilitate understanding of the part according to the technique of the present disclosure, in the described contents and illustrated contents, descriptions of technical knowledge and the like that do not require particular explanations to enable implementation of the technique of the present disclosure are omitted.

What is claimed is:

1. An information processing apparatus that predicts a quality of a product obtained by a process including one or more pieces of processing, through each piece of processing an object to be processed becoming a processed object, the apparatus comprising:
at least one processor configured to
acquire, in at least one piece of processing of the process, at least one piece of chemical information of the object to be processed before the processing as well as at least one piece of chemical information of the processed object after the processing, acquire a calculation value of a difference between numerical values that are obtained from the at least one piece of chemical information of the object to be processed before the processing and the at least one piece of chemical information of the processed object after the processing, and
set the difference as an explanatory variable, set the quality of the product as an objective variable, and predict the quality of the product based on the calculation value by using a trained model obtained by performing machine learning based on a known data set of the explanatory variable and the objective variable,
wherein the trained model is trained based on a quality of the product produced by a flow processing device that has at least one processing unit corresponding to each of the at least one piece of processing and a difference for learning that is a first difference between numerical values that are obtained from the at least one piece of chemical information obtained from the object to be processed before the processing performed in each of the at least one processing unit and at least one piece of chemical information obtained from the processed object after the process performed in each of the at least one processing unit, and
the prediction of the quality of the product is used for searching for a processing condition of the flow processing device.

2. The information processing apparatus according to claim 1,
wherein the processor is configured to
acquire a condition value of the processing condition for the at least one piece of processing of the process,
set the explanatory variable to include the processing condition in addition to the difference, and
predict the quality of the product based on the calculation value and the condition value in the prediction of the quality of the product.

3. The information processing apparatus according to claim 1,
wherein the processor is configured to acquire, in the acquisition of the information, a spectroscopic spectrum as the chemical information in the at least one piece of processing of the process.

4. The information processing apparatus according to claim 3,
wherein the processor is configured to acquire, in the acquisition of the calculation value, the calculation value of an intensity at a wave number or the calculation value of an integrated intensity in a wave number region, the wave number and the wave number region being a characteristic wave number and a characteristic wave number region in the spectral spectrum changed by the at least one piece of processing.

5. The information processing apparatus according to claim 4,
wherein the processor is configured to determine the wave number or the wave number region based on a quantum chemical calculation.

6. The information processing apparatus according to claim 4,
wherein the characteristic wave number or the characteristic wave number region includes a wave number or a wave number region derived from a by-product.

7. The information processing apparatus according to claim 1,
wherein the processor further acquires further the at least one piece of physical information of the object to be processed before the processing as well as at least one piece of physical information of the processed object before processing, and
further acquires a calculated value of a difference between numerical values obtained from the at least one piece of physical information of the object to be processed before processing and the at least one piece of physical information of the processed object after processing, and
the trained model is trained based on the quality of the product produced by the flow processing device and a difference for learning that includes a first difference and a second difference between numerical values that are obtained from the at least one piece of physical information obtained from the object to be processed before the processing performed in each of the at least one processing unit and the at least one piece of physical information obtained from the processed object after the process performed in each of the at least one processing unit.

8. The information processing apparatus according to claim 7,
wherein the at least one piece of processing of the process is flow processing using a flow path, and
the processor is configured to acquire, in the acquisition of the information, a state quantity of a flow field as the physical information of the flow processing.

9. The information processing apparatus according to claim 8,
wherein the processor is configured to acquire, in the acquisition of the information, the state quantity of the flow field by a computational fluid dynamics analysis.

10. The information processing apparatus according to claim 9,
wherein the flow processing is processing of mixing a plurality of fluids, and
the state quantity of the flow field is a mixing ratio of the fluids that is calculated based on the computational fluid dynamics analysis.

11. An information processing method that predicts a quality of a product obtained by a process including one or more pieces of processing, through each piece of processing an object to be processed becoming a processed object, the method comprising:

acquiring, in at least one piece of processing of the process, at least one piece of chemical information of the object to be processed before the processing as well as at least one piece of chemical information of the processed object after the processing;

acquiring a calculation value of a difference between numerical values that are obtained from the at least one piece of chemical information of the object to be processed before the processing and the at least one piece of chemical information of the processed object after the processing; and setting the difference as an explanatory variable, setting the quality of the product as an objective variable, and predicting the quality of the product based on the calculation value by using a trained model obtained by performing machine learning based on a known data set of the explanatory variable and the objective variable, wherein the trained model is trained based on a quality of the product produced by a flow processing device that has at least one processing unit corresponding to each of the at least one piece of processing and a difference for learning that is a first difference between numerical values that are obtained from the at least one piece of chemical information obtained from the object to be processed before the processing performed in each of the at least one processing unit and at least one piece of chemical information obtained from the processed object after the process performed in each of the at least one processing unit, and the prediction of the quality of the product is used for searching for a processing condition of the flow processing device.

12. A non-transitory computer-readable storage medium storing therein a program causing a computer to execute information processing of predicting a quality of a product obtained by a process including one or more pieces of processing, through each piece of processing an object to be processed becoming a processed object, the information processing comprising:

acquiring, in at least one piece of processing of the process, at least one piece of chemical information of the object to be processed before the processing as well as at least one piece of chemical information of the processed object after the processing;

acquiring a calculation value of a difference between numerical values that are obtained from the at least one piece of chemical information of the object to be processed before the processing and the at least one piece of chemical information of the processed object after the processing; and setting the difference as an explanatory variable, setting the quality of the product as an objective variable, and predicting the quality of the product based on the calculation value by using a trained model obtained by performing machine learning based on a known data set of the explanatory variable and the objective variable, wherein the trained model is trained based on a quality of the product produced by a flow processing device that has at least one processing unit corresponding to each of the at least one piece of processing and a difference for learning that is a first difference between numerical values that are obtained from the at least one piece of chemical information obtained from the object to be processed before the processing performed in each of the at least one processing unit and at least one piece of chemical information obtained from the processed object after the process performed in each of the at least one processing unit, and the prediction of the quality of the product is used for searching for a processing condition of the flow processing device.

* * * * *